US011952599B2

(12) United States Patent
Rex et al.

(10) Patent No.: US 11,952,599 B2
(45) Date of Patent: Apr. 9, 2024

(54) SINGLE ADENO-ASSOCIATED VIRUS (AAV)-SIZED NUCLEOTIDE FOR USE IN CRISPR INTERFERENCE OR ACTIVATION

(71) Applicant: Vanderbilt University, Nashville, TN (US)

(72) Inventors: Tonia S. Rex, Nashville, TN (US); Jon R. Backstrom, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 84 days.

(21) Appl. No.: 17/150,562

(22) Filed: Jan. 15, 2021

(65) Prior Publication Data

US 2021/0222139 A1     Jul. 22, 2021

Related U.S. Application Data

(60) Provisional application No. 62/962,679, filed on Jan. 17, 2020.

(51) Int. Cl.
  *C12N 9/22*       (2006.01)
  *C12N 15/11*      (2006.01)
  *C12N 15/86*      (2006.01)

(52) U.S. Cl.
  CPC .............. *C12N 9/22* (2013.01); *C12N 15/11* (2013.01); *C12N 15/86* (2013.01); *C12N 2310/20* (2017.05); *C12N 2750/14143* (2013.01); *C12N 2800/80* (2013.01)

(58) Field of Classification Search
  CPC .......... C12N 9/22; C12N 15/11; C12N 15/86; C12N 2310/20; C12N 2750/14143; C12N 2800/80; C12N 15/113; C12N 2830/002; C12N 2830/005
  See application file for complete search history.

(56) References Cited

U.S. PATENT DOCUMENTS

2018/0312824 A1* 11/2018 Zhang ................. C12N 15/102

OTHER PUBLICATIONS

Arimbasseri et al.(Comparative overview of RNA polymerase II and III transcription cycles, with focus on RNA polymerase III termination and reinitiation. Transcription, vol. 5, Dec. 2013) (Year: 2013).*
Hajizadeh Dastjerdi et al. (The Expanding Class 2 CRISPR Toolbox: Diversity, Applicability, and Targeting Drawbacks. BioDrugs 33 , 2019) (Year: 2019).*
Zhao P, Zhang Z, Lv X, Zhao X, Suehiro Y, Jiang Y, Wang X, Mitani S, Gong H, Xue D. One-step homozygosity in precise gene editing by an improved CRISPR/Cas9 system. Cell Res. May 2016;26(5):633-6. doi: 10.1038/cr.2016.46. Epub Apr. 8, 2016. PMID: 27055372; Pmcid: PMC4856768. (Year: 2016).*
Addgene Plasmid #61594 Sequence/Vector map (Year: 2015).*
Chen et al (Fusion Protein Linkers: Property, Design and Functionality. Adv Drug Deliv Rev, vol. 65, Oct. 2013) (Year: 2013).*
Arai et al (Design of linkers which effectively separate domains of a bifunctional fusion protein. Protein Engineering, vol. 14, 2001) (Year: 2001).*
Bellefroid, E.J., Poncelet, D.A., Lecocq, P.J., Revelant, O., and Martial, J.A. (1991). The evolutionarily conserved Krüppel-associated box domain defines a subfamily of eukaryotic multifingered proteins. Proc. Natl. Acad. Sci. USA 88, 3608-3612.
Margolin, J.F., Friedman, J.R., Meyer, W.K.-H., Vissing, H., Thiesen, H .- J., and Rauscher, F.J., 3rd (1994). Krüppel-associated boxes are potent transcriptional repression domains. Proc. Natl. Acad. Sci. USA 91, 4509-4513.
Witzgall, R., O'Leary, E., Leaf, A., Önaldi, D., and Bonventre, J.V. (1994). The Krüppel-associated box-A (KRAB-A) domain of zinc finger proteins mediates transcriptional repression. Proc. Natl. Acad. Sci. USA 91, 4514-4518.
Thakore, P.I., Kwon, J.B., Nelson, C.E., Rouse, D.C., Gemberling, M.P., Oliver, M.L., and Gersbach, C.A. (2018). RNA-guided transcriptional silencing in vivo with S. aureus CRISPR-Cas9 repressors. Nat. Commun. 9, 1674-1682.
Li, C., and Samulski, R.J. (2020). Engineering adeno-associated virus vectors for gene therapy. Nat. Rev. Genet. 21, 255-272.
Lau, C.-H., Ho, J.W.-T., Lo, P.K., and Tin, C. (2019). Targeted transgene activation in the brain tissue by systemic delivery of engineered AAV1 expressing CRISPRa. Mol. Ther. Nucleic Acids 16, 637-649.
Marqusee, S., and Baldwin, R.L. (1987). Helix stabilization by Glu- . . . Lys+ salt bridges in short peptides of de novo design. Proc. Natl. Acad. Sci. USA 84, 8898-8902.
Nishimasu, H., Cong, L., Yan, W.X., Ran, F.A., Zetsche, B., Li, Y., Kurabayashi, A., Ishitani, R., Zhang, F., and Nureki, O. (2015). Crystal structure of *Staphylococcus aureus* Cas9. Cell 162, 1113-1126.
Ivics, Z., Hackett, P.B., Plasterk, R.H., and Izsvák, Z. (1997). Molecular reconstruction of Sleeping Beauty, a Tc1-like transposon from fish, and its transposition in human cells. Cell 91, 501-510.
Mátés, L., Chuah, M.K., Belay, E., Jerchow, B., Manoj, N., Acosta-Sanchez, A., Grzela, D.P., Schmitt, A., Becker, K., Matrai, J., et al. (2009). Molecular evolution of a novel hyperactive Sleeping Beauty transposase enables robust stable gene transfer in verte brates. Nat. Genet. 41, 753-761.

(Continued)

*Primary Examiner* — Valarie E Bertoglio
*Assistant Examiner* — Matasha Dhar
(74) *Attorney, Agent, or Firm* — Stites & Harbison PLLC; Mandy Wilson Decker

(57) ABSTRACT

A nucleic acid molecule is uniquely designed and encodes an entire CRISPRi or CRISPRa system, while being sized for packaging within a single adeno-associated virus (AAV) vector. Examples of the nucleic acid molecule include about 4600 to 4700 base pairs. Examples of the nucleic acid molecule can include a nucleotide encoding a Cas polypeptide; a nucleotide encoding a repressor or an activator domain attached to the nucleotide encoding the Cas polypeptide via a linker; a first promoter operably connected to the nucleotide encoding the repressor or activator domain or the nucleotide encoding the Cas polypeptide; a nucleotide encoding an alpha-helical connecting the nucleotide encoding the Cas polypeptide to a nuclear localization signal (NLS); and a second promoter operably connected to a guide RNA (gRNA).

17 Claims, 8 Drawing Sheets
Specification includes a Sequence Listing.

(56) References Cited

OTHER PUBLICATIONS

Kowarz, E., Löscher, D., and Marschalek, R. (2015). Optimized Sleeping Beauty trans-posons rapidly generate stable transgenic cell lines. Biotechnol. J. 10, 647-653.

Gao, Z., Herrera-Carrillo, E., and Berkhout, B. (2018). Delineation of the exact tran-scription termination signal for type 3 polymerase III. Mol. Ther. Nucleic Acids 10, 36-44.

Kramer, M.G., Barajas, M., Razquin, N., Berraondo, P., Rodrigo, M., Wu, C., Qian, C., Fortes, P., and Prieto, J. (2003). In vitro and in vivo comparative study of chimeric liver-specific promoters. Mol. Ther. 7, 375-385.

Kleinstiver, B.P., Prew, M.S., Tsai, S.Q., Topkar, V.V., Nguyen, N.T., Zheng, Z., Gonzales, A.P., Li, Z., Peterson, R.T., Yeh, J.R., Aryee, M.J., et al. (2015). Engineered CRISPR-Cas9 nucleases with altered PAM specificities. Nature 523, 481-485.

Ran, F.A., Cong, L., Yan, W.X., Scott, D.A., Gootenberg, U.S., Kriz, A.J., Zetsche, B., Shalem, O., Wu, X., Makarova, K.S., et al. (2015). In vivo genome editing using *Staphylococcus aureus* Cas9. Nature 520, 186-191.

Melén, K., Kinnunen, L., Fagerlund, R., Ikonen, N., Twu, K.Y., Krug, R.M., and Julkunen, I. (2007). Nuclear and nucleolar targeting of influenza A virus NS1 protein: striking differences between different virus subtypes. J. Virol. 81, 5995-6006.

Mekhail, K., Rivero-Lopez, L., Al-Masri, A., Brandon, C., Khacho, M., and Lee, S. (2007). Identification of a common subnuclear localization signal. Mol. Biol. Cell 18, 3966-3977.

Spolitu, S., Okamoto, H., Dai, W., Zadroga, J.A., Wittchen, E.S., Gromada, J., and Ozcan, L. (2019). Hepatic glucagon signaling regulates PCSK9 and low-density lipo-protein cholesterol. Circ. Res. 124, 38-51.

Kleinstiver, B.P., Prew, M.S., Tsai, S.Q., Nguyen, N.T., Topkar, V.V., Zheng, Z., and Joung, J.K. (2015). Broadening the targeting range of *Staphylococcus aureus* CRISPR-Cas9 by modifying PAM recognition. Nat. Biotechnol. 33, 1293-1298.

Ye, L., Wang, J., Tan, Y., Beyer, A.I., Xie, F., Muench, M.O., and Kan, Y.W. (2016). Genome editing using CRISPR-Cas9 to create the HPFH genotype in HSPCs: An approach for treating sickle cell disease and b-thalassemia. Proc. Natl. Acad. Sci. USA 113, 10661-10665.

Gao, Z., Harwig, A., Berkhout, B., and Herrera-Carrillo, E. (2017). Mutation of nucle-otides around the +1 position of type 3 polymerase III promoters: The effect on tran-scriptional activity and start site usage. Transcription 8, 275-287.

Boque-Sastre, R. et al. Head-to-head antisense transcription and R-loop formation promotes transcriptional activation. Proc. Natl. Acad. Sci. USA 112, 5785-5790 (2015).

\* cited by examiner

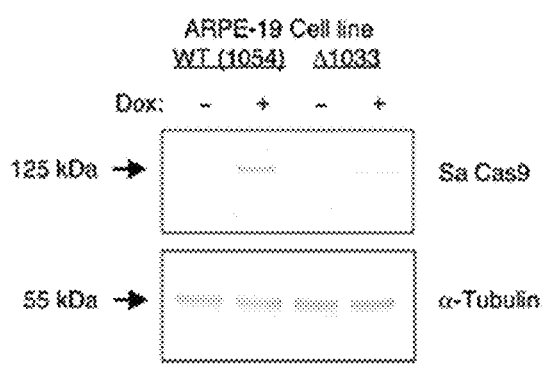
FIG. 1A
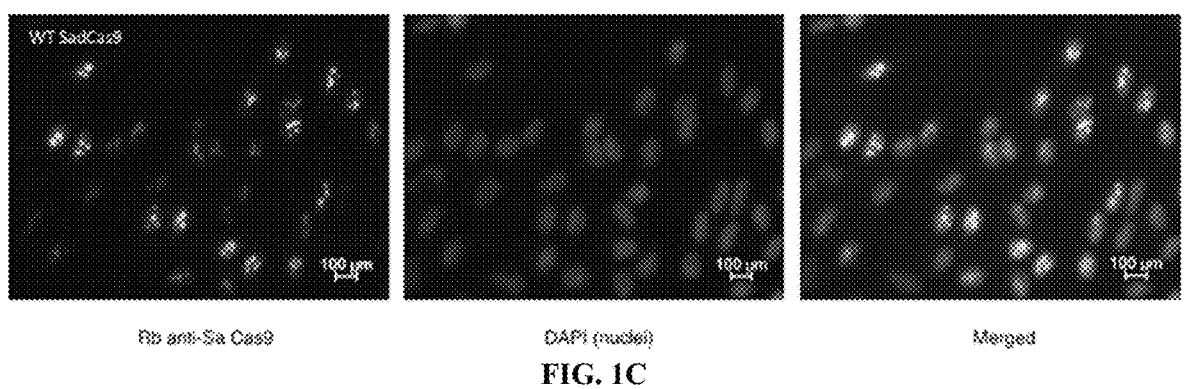
FIG. 1B
FIG. 1C

SINGLE ADENO-ASSOCIATED VIRUS (AAV)-SIZED NUCLEOTIDE FOR USE IN CRISPR INTERFERENCE OR ACTIVATION

RELATED APPLICATIONS

This application claims priority from U.S. Provisional Application Ser. No. 62/962,679 filed Jan. 17, 2020, the entire disclosure of which is incorporated herein by this reference.

GOVERNMENT INTEREST

This invention was made with government support under grant numbers W81XWH-15-1-0096 and W81XWH-17-2-0055, awarded by the Department of the Army, and EY022349, NS094595, EY29893, and EY008126 awarded by the National Institutes of Health. The government has certain rights in the invention.

TECHNICAL FIELD

The presently-disclosed subject matter generally relates to a CRISPR-based transcription-regulation system. In particular, certain embodiments of the presently-disclosed subject matter relate to a nucleic acid molecule encoding the entire CRISPR interference (CRISPRi) or an entire CRISPR activation (CRISPRa) system, designed to be within the optimal size for being packaged within a single adeno-associated virus (AAV) vector.

INTRODUCTION

Catalytically inactive Cas, such as dCas9, fused to an effector domain has the potential to be a powerful, clinically relevant tool for regulating transcription, particularly if delivered in the relatively cell-type selective, non-replicative, and clinically safe adeno-associated virus (AAV).[1-3]

AAV has a number of advantages such as, for example, capsid serotype increases targeting specificity, it is unable to replicate, it does not integrate into the genome of post-mitotic cells, and it is FDA-approved and clinically available for the treatment of, for example, Lebers Congenital Amaurosis due to mutations in Rpe65.

Due to the ~4.7 kb packaging size limitation of AAV, *Staphylococcus aureus* deactivated Cas9 (SadCas9) is a good candidate for this approach. Although SadCas9 is one of the smallest known double-stranded DNA-directed Cas proteins, it requires 3.2 kb of DNA. Addition of a fused effector domain to modulate transcription along with promoter and poly(A) regions leaves very little space for additional elements.

Thus, the gold standard for delivery of functional CRISPR machinery requires two AAV particles: one with SadCas9-KRAB and the other with a U6 polymerase promoter driving expression of a guide RNA (gRNA) that targets a gene of interest.[4] Transduction of the liver with this dual AAV achieved impressive knockdown of serum protein convertase subtilisin/kexin type 9 (Pcsk9). Unfortunately, AAV is a relatively inefficient virus for transducing many cells in vivo and the likelihood of getting both vectors in sufficient numbers of relevant cells for treatment efficacy in more complex tissues is very low (for review see Li and Samulski[5]).

Thus, Despite the benefits of the currently-available systems, there are various disadvantages with requiring multiple AAVs. Particularly, AAV is inefficient, particularly for transductions of neurons. The likelihood of transducing sufficient numbers of cells to enact a clinical effect with multiple AAVs is extremely low. Higher titers of AAV would be needed, decreasing the safety of the approach. Yet, the size constraints of AAV have heretofore prevented the development of a single AAV system.

One previous study packaged the components of CRISPR activation (CRISPRa) into a single AAV and was successful in activating expression of an exogenous, overexpressed target.[6] However, this system was inefficient at modulating expression of an endogenous gene. Their CRISPRa system required three gRNAs and their CRISPRi system reduced expression of an endogenous target gene only 14% in vitro.

CRISPR-based studies, whether gene editing (CRISPR) or epigenetic modification through interference (CRISPRi) or activation (CRISPRa) of gene expression typically rely on the high expression-level CMV promoter. Nonetheless, CMV is too large (700 bp) to include in a functional CRISPRi or CRISPRa construct for packaging in AAV, which is the only FDA-approved viral vector. The downside is that selecting either a general or more tissue-selective promoter that is smaller (<370 bp) would likely result in lower mRNA levels relative to cytomegalovirus (CMV). It was reasoned that although levels attained with CMV are probably more than is required for functional responses, significantly lower protein levels would require strategically designed nuclear targeting, the location of KRAB within *Staphylococcus aureus* dCas9 (SadCas9), and the promoter for sgRNA.

As disclosed herein, the present inventors have developed a unique design and strategy in which the entire CRISPR system surprisingly can be included in a single AAV genome, and results in higher nuclear levels of Cas than previously achieved. This system beneficially allows modulation of gene expression after transduction of one AAV type into cells of interest, and is effective at modulating expression of an endogenous gene in vivo.

SUMMARY

The presently-disclosed subject matter meets some or all of the above-identified needs, as will become evident to those of ordinary skill in the art after a study of information provided in this document.

The present invention provides an improved system for nuclear targeting of a Cas polypeptide and successfully knocking down expression of an endogenous gene using a sgRNA both in vitro and in vivo.

Embodiments of the presently-disclosed subject matter include a complete CRISPR construct packaged into a single AAV. Subsequent modifications of this CRISPR construct for other studies would entail selecting a <370 bp promoter or Cas that is active in the desired cell-type and the appropriate gRNA. Some embodiments of a CRISPRi system, as disclosed herein, include SadCas9 nuclear targeting and KRAB fusion, as well as promoter size and selection, designed to result in a single AAV vector that contains all functional CRISPRi components. In one exemplary embodiment, the Pcsk9 gRNA was used, as disclosed herein.[4] The construct was packaged into liver-tropic AAV2/8 and demonstrated nuclear localization of KRAB-SadCas9 (N-KRAB) in liver cells and knock-down of Pcsk9.

The presently disclosed subject matter includes a nucleic acid including a CRISPRi or a CRISPRa system. In some embodiments, the nucleic acid includes about 4600 to 4700 base pairs. The presently disclosed subject matter further includes a vector comprising the nucleic acid. In some embodiments, the vector is an adeno-associated virus (AAV) vector.

In some embodiments, the nucleic acid comprises a nucleotide encoding a Cas polypeptide; a nucleotide encoding a repressor domain or an activator domain attached to the nucleotide encoding the Cas polypeptide via a first linker consisting of 6 to about 60 amino acids; a first promoter operably connected to the nucleotide encoding the repressor or activator domain or the nucleotide encoding the Cas polypeptide; a second linker that is alpha-helical and consists of about 15 to about 22 amino acids connecting the Cas polypeptide to a nuclear localization signal (NLS); and a second promoter operably connected to a guide RNA (gRNA).

In some embodiments of the presently-disclosed subject matter, the Cas polypeptide is a Cas9 polypeptide. In some embodiments, the Cas9 polypeptide is an SaCas9 polypeptide. In some embodiments, the Cas9 polypeptide comprises the amino acid sequence of SEQ ID NO: 1. In some embodiments, the Cas9 polypeptide comprises the amino acid sequence of SEQ ID NO: 3.

In some embodiments of the presently-disclosed subject matter, the Cas polypeptide is a Cas12 polypeptide. In some embodiments, the Cas12 polypeptide is an SaCas12 polypeptide. In some embodiments, the Cas12 polypeptide is an SaCas12H polypeptide.

In some embodiments of the presently-disclosed subject matter, the nucleic acid molecule includes an activator domain. In some embodiments, the nucleic acid molecule includes a repressor domain. In some embodiments, the repressor domain is selected from the group consisting of KRAB, SRDX, MAD1, and TIEG1.

In some embodiments of the presently-disclosed subject matter, the linker attaching the nucleotide encoding the repressor domain to the nucleotide encoding the Cas polypeptide consists of 6 to about 60 nucleotides. In some embodiments, the linker consists of about 7 amino acids.

In some embodiments of the presently-disclosed subject matter, the first promoter is an RNA polymerase II promoter of about 25 to about 400 nucleotides (base pairs) in length. In some embodiments, the first promoter is about 350 to about 375 nucleotides in length.

In some embodiments of the presently-disclosed subject matter, the second linker, which is an alpha-helical linker, comprises a nucleotide encoding the sequence of SEQ ID NO: 9 or SEQ ID NO: 10. In some embodiments of the presently-disclosed subject matter, the NLS has a sequence selected from the group consisting of SEQ ID NO: 11 and SEQ ID NO: 12.

In some embodiments of the presently-disclosed subject matter, the second promoter is an RNA polymerase II promoter of about 150-250 nucleotides (base pairs) in length.

In some embodiments of the presently-disclosed subject matter, the nucleic acid further comprises a polyA domain.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

FIGS. 1A-1C. Analysis of SadCas9. (FIG. 1A) Effect of carboxyl-terminal truncations on nuclear targeting of SadCas9. All constructs had the EA linker and the myc-NLS at the extreme carboxyl-terminus (Table 1). The sequence begins at $Arg^{1015}$ ("O") and locations of b-structure are marked above the protein sequence (adapted from Nishimasu et al.[8]). Asterisks (**) denote a significant difference (p<0.01) between WT and D1,036 SadCas9. (FIG. 1B) Blot of extracts from ARPE-19 cell lines expressing WT or D1033 SadCas9 grown in the absence or presence of 5 μg Dox/mL. (FIG. 1C) ARPE-19 polyclonal cell line expressing WT SadCas9 (5 Dox/mL) displayed punctate labeling (green) within nuclei (blue).

(FIG. 2A) The FLAG-tag was used to examine accessibility of the amino-terminal "domain" of SadCas9. Immunoreactive FLAG was barely detected with a single threonine residue between FLAG and SadCas9 (upper left panel) but was greatly enhanced with the 7-amino acid GS linker (lower left panel) and co-localized with immunoreactive SadCas9 (lower right panel). Therefore, the GS linker was used for the KRAB-SadCas9 (N-KRAB) construct. (FIG. 2B) Nuclear localization of N-KRAB in an ARPE-19 cell line that was treated with 5 μg Dox/mL. (FIG. 2C) Blot of immunoreactive SadCas9 proteins from the ARPE-19 cell lines. The N-KRAB construct migrated to a position between C-KRAB (lane 1) and SadCas9 at −125 kDa (lane 3). The internal KRAB (I-KRAB) construct displayed significantly lower protein levels than the other constructs and was only detected by immunoprecipitation.

FIG. 3A. A molecular basis for the smaller than expected apparent mass of N-KRAB (FIG. 2C) was first examined with truncated (-tr) SadCas9 constructs. The predicted 8 kDa difference in mass was greater than the observed 4 kDa difference between SadCas9-tr (45 kDa) and N-KRAB-tr (49 kDa). Translation was not occurring at a downstream methionine since mutation of the first two methionine residues of N-KRAB-tr (M34A/M71A) did not increase the mass of N-KRAB-tr. The 45 kDa bands from N-KRAB-tr are due to cleavage at both the amino- and carboxyl-terminus. FIG. 3B. Full-length HA-tagged SadCas9 (HA-SadCas9) or N-KRAB (HA-N-KRAB) proteins were immunoprecipitated with mouse anti-Sa Cas9 and blots probed with either rabbit anti-Sa Cas9 (top panel) or rabbit anti-HA (bottom panel). HA-N-KRAB has a larger apparent mass than HA-SadCa9. FIG. 3C. HA-N-KRAB was detected with HA-tag antibodies in nuclei of mouse liver AML-12 cells.

FIG. 4A. Location of VIMENTIN gRNAs relative to the translation ATG start site. FIG. 4B. A Sleeping Beauty ARPE-19 cell line expressing N-KRAB without gRNA was transiently-transfected with a guide RNA (gRNA) plasmid that co-expresses ZsGreen and labeled with anti-vimentin. The U6 promoter of the introduced plasmid was driving expression of either non-targeting (NT) or VIMENTIN(C5) gRNA. FIG. 4C. Example of results that quantitated fluorescence of immunoreactive vimentin per cell from the N-KRAB cell line. Green fluorescence was used to identify cells that express gRNA and the red fluorescence was measured using the imaging application ImageJ from at least 100 cells per experiment. The results (mean±s.d.) are representative of at least two independent experiments for each gRNA. The asterisk (*) denotes a significant difference (P<0.05) between cells expressing NT vs. C5 gRNA. FIG. 4D. The C5 gRNA plasmid did not significantly decrease levels of vimentin immunoreactivity in the C-KRAB cell line. FIG. 4E. Sleeping Beauty cell lines co-expressing 7SK:C5 gRNA were analyzed for vimentin protein levels. Blots of SDS-soluble protein (1 µg) were probed with antibodies against vimentin (top panel) or actin (lower panel). FIG. 4F. Normalization of immoreactive vimentin to actin from three independent experiments (mean±s.d.) revealed that N-KRAB decreased levels of vimentin 2-fold (P<0.01) relative to parental cells.

(FIG. 5A) Blot of soluble extracts from parental AML-12 mouse liver cells and cell lines expressing SadCas9, N-KRAB, or C-KRAB treated with 5 µg Dox/mL. The N-KRAB and C-KRAB constructs co-expressed U6-driven non-targeting (NT) or Pcsk9 gRNA. (FIG. 5B) Both N-KRAB and C-KRAB were localized exclusively in the nucleus. Results in FIGS. 5A and 5B are representative of two independent experiments. (FIG. 5C) Levels of Pcsk9 from the supernatant of cells. Relative to parental cells, cells with SadCas9 decreased Pcsk9 levels 2-fold (**p<0.01). A comparison of NT versus Pcsk9 gRNA revealed a significant difference (*p<0.05) for N-KRAB, but not C-KRAB. The results (mean±SD) are representative of three independent experiments.

(FIG. 6A) Blot of soluble protein from cell lines probed with antibodies against Sa Cas9 (top panel) or a-tubulin (bottom panel). The results are representative of two independent experiments. (FIG. 6B) Analysis of mRNA levels for N-KRAB relative to Gapdh [DCt=(Ct SadCas9)−(Ct Gapdh)]. (FIG. 6C) Levels of Pcsk9 mRNA relative to parental cells. The U6 promoter and Pcsk9 gRNA reduced levels of Pcsk9 mRNA 3.5-fold relative to gStop (p<0.01), whereas there was no difference for the 7SK promoter. (FIG. 6D) Quantitation of Pcsk9 protein from the cell supernatants. A comparison between promoters with gStop gRNA was not significant, whereas promoters with Pcsk9 gRNA revealed that the U6 promoter decreased Pcsk9 levels 2.5-fold relative to the 7SK promoter (p<0.01). The results (mean±SD) presented in (FIG. 6B)-(FIG. 6D) are representative of three independent experiments.

(FIG. 7A) Analysis of N-KRAB mRNA levels from the different promoters (see Table 2) relative to cells with CMV and U6:gStop. Levels of N-KRAB mRNA from the tested promoters were significantly lower than CMV (°°p<0.01). (FIG. 7B) Pcsk9 mRNA levels and (FIG. 7C) Pcsk9 protein levels relative to parental AML-12 cells. The results (mean±SD) are representative of three independent experiments. Asterisks denote significance at p<0.05 (°) or p<0.01 (°°) relative to parental cells.

(FIG. 8A) Diagram of a representative AAV2 plasmid construct used to package AAV8.N-KRAB. The promoters included Alb-AAT or EF-1 (see Table 2) with either gStop or Pcsk9 gRNA. (FIG. 8B) Fold-increase in N-KRAB mRNA from different doses of rAAV.N-KRAB.Pcsk9 under control the Alb-AAT promoter relative to the EF-1 promoter at a dose of $2\times10^{11}$ vg/mouse. The results are from one experiment and asterisks (**) denote p<0.01. Mice tail-injected with PBS or Alb-AAT viruses with either gStop or Pcsk9 gRNA at doses of $2\times10^{11}$ vg/mouse were evaluated for (FIG. 8C) levels of Pcsk9 mRNA relative to control PBS mice and (FIG. 8D) concentration of Pcsk9 from sera. The results presented in FIGS. 8C and 8D are representative of two independent experiments and asterisks denote p<0.05 (*) or p<0.01 (**). (FIG. 8E) Immunolabeling of liver sections from mice treated with either $2\times10^{11}$ vg/mouse of AAV8.N-KRAB (Pcsk9; top panels) or PBS (bottom panels). Sections were labeled with rabbit anti-Sa Cas9 (left panels) and DAPI (middle panels). The arrows denote nuclear labeling of N-KRAB. The results are representative of three animals from each treatment.

BRIEF DESCRIPTION OF THE SEQUENCE LISTING

Figure 2A:
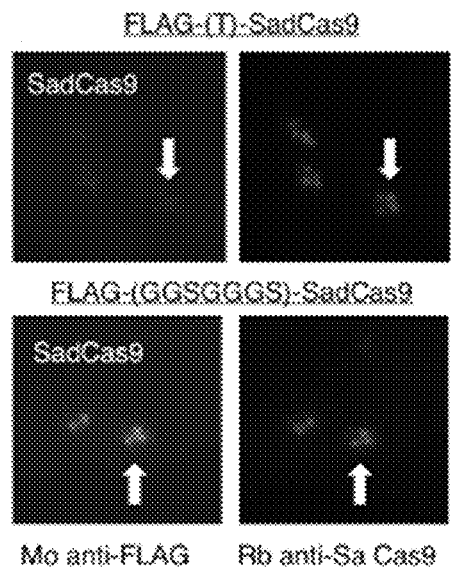
FIGS. 2A-2C. Analysis of SadCas9 Constructs with the Transcriptional Repression a Krüppel associated box carboxyl-terminus (KRAB) Domain.

SEQ ID NO: 1 is an amino acid sequence of an exemplary Cas polypeptide according to the presently-disclosed subject matter.

SEQ ID NO: 2 is a nucleic acid sequence encoding an exemplary Cas polypeptide according to the presently-disclosed subject matter.

SEQ ID NO: 3 is an amino acid sequence of an exemplary Cas polypeptide according to the presently-disclosed subject matter.

SEQ ID NO: 4 is a nucleic acid sequence encoding an exemplary Cas polypeptide according to the presently-disclosed subject matter.

SEQ ID NO: 5 is an amino acid sequence of an exemplary Cas polypeptide according to the presently-disclosed subject matter.

SEQ ID NO: 6 is a nucleic acid sequence encoding an exemplary Cas polypeptide according to the presently-disclosed subject matter.

SEQ ID NO: 7 is an amino acid sequence of an exemplary repressor domain according to the presently-disclosed subject matter.

SEQ ID NO: 8 is a nucleic acid sequence encoding an exemplary repressor domain according to the presently-disclosed subject matter.

SEQ ID NO: 9 is an amino acid sequence of an exemplary alpha-helical linker according to the presently-disclosed subject matter.

SEQ ID NO: 10 is an amino acid sequence of an exemplary alpha-helical linker according to the presently-disclosed subject matter.

SEQ ID NO: 11 is an amino acid sequence of an exemplary nuclear localization signal according to the presently-disclosed subject matter.

SEQ ID NO: 12 is an amino acid sequence of an exemplary nuclear localization signal according to the presently-disclosed subject matter.

SEQ ID NO: 13 is a nucleic acid sequence of an exemplary first promoter according to the presently-disclosed subject matter.

SEQ ID NO: 14 is a nucleic acid sequence of an exemplary second promoter according to the presently-disclosed subject matter.

SEQ ID NO: 15 is a nucleic acid sequence of an exemplary nucleotide capable of being received within a single adeno-associated virus vector, according to the presently-disclosed subject matter.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes a unique design and strategy for creating system in which the entire CRISPRi system can be included in a single AAV genome.

The presently-disclosed subject matter includes a nucleic acid molecule encoding the entire CRISPRi system, designed to be within the optimal size for being packaged within a single adeno-associated virus (AAV) vector. In some embodiments, the nucleic acid molecule is 4.7 kb or smaller (including both inverted terminal repeats). In some embodiments, the nucleic acid molecule consists of about 4600 to 4700 base pairs.

In some embodiments, the nucleic acid molecule includes: (a) a nucleotide encoding a Cas polypeptide; (b) a nucleotide encoding a repressor domain attached to the nucleotide encoding the Cas polypeptide via a first linker consisting of 6 to about 60 nucleotides; (c) a first promoter operably connected to the nucleotide encoding the repressor domain or the nucleotide encoding the Cas polypeptide; (d) a nucleotide encoding a second linker that is alpha-helical and consists of about 15 to about 22 amino acids connecting the nucleotide encoding the Cas polypeptide to a nuclear localization signal (NLS); and (e) a second promoter operably connected to a guide RNA (gRNA).

Any Cas polypeptide can be selected, with consideration to size and desired application of the system. For example, in some embodiments, the Cas polypeptide includes the same or fewer number of amino acids as compared to *Staphylococcus aureus* Cas9 (SaCas9).

In some embodiments, the Cas polypeptide is catalytically inactive Cas (dCas). In some embodiments, the Cas polypeptide is a Cas9 polypeptide. In some embodiments, the Cas9 polypeptide is an SaCas9 polypeptide. In some embodiments, the Cas9 polypeptide comprises the amino acid sequence of RIIKTIASKTQSIKKYSTDILGNLYEVKSKKH (SEQ ID NO: 1). In some embodiments, the Cas9 polypeptide comprises the amino acid sequence of RIIKTIASKTQSIKKYSTDILGNLYEVKSKKHPQIIKKG (SEQ ID NO: 3). In some embodiments, the Cas polypeptide is a Cas12 polypeptide. In some embodiments, the Cas12 polypeptide is an SaCas12 polypeptide. In some embodiments, the Cas12 polypeptide is an SaCas12H polypeptide.

Examples or relevant Cas polypeptides include, but are not limited to, Cas1, Cas1B, Cas2, Cas3, Cas4, Cas5, Cash, Cas7, Cas8, Cas9, Cas10, Cas11, Cas12, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cpf1 polypeptide.

CRISPRi makes use of a Cas polypeptide or Cas polypeptide bound to repressor that, together with a guide RNA, repress or decrease transcription of a target gene. As noted above, the nucleic acid molecule can include a repressor domain. The repressor domain can be, for example, a Krüppel associated box (KRAB) domain. In some embodiments, the repressor can be domains from SRDX, MAD1, or TIEG1.

In some embodiments, the repressor domain is attached to the amino-terminal end of the Cas polypeptide. In some embodiments of the nucleic acid molecule, the linker attaching the nucleotide encoding the repressor domain to the nucleotide encoding the Cas polypeptide consists of 6 to about 60 nucleotides. In some embodiments, the linker consists of about 6, 7, 8, 9, 10, 11, 12, 13, 14, 15, 16, 17, 18, 19, 20, 21, 22, 23, 24, 25, 26, 27, 28, 29, or 30 nucleotides.

In some embodiments of the nucleic acid molecule, the first promoter is operably connected to the nucleotide encoding the repressor domain. In some embodiments, the first promoter an RNA polymerase II promoter of about 25 to about 400 nucleotides in length. In some embodiments, the first promoter is about 350 to about 375 nucleotides in length. In some embodiments, the first promoter optionally includes an enhancer. As is well-known in the art, a promoter is a nucleotide sequence where transcription of an operatively-connected gene is initiated. Promoters can include an RNA polymerase binding site and transcription factor binding sites. In some cases, an enhancer is additionally provided. As is well-known in the art, an enhancer is a nucleotide sequence that can be bound by transcription factors and activators to enhance likelihood of transcription of an operatively-connected gene.

As noted above, the nucleic acid molecule includes a second linker that is alpha-helical, connecting the nucleotide encoding the Cas polypeptide to a nuclear localization signal (NLS). The NLS can direct a Cas polypeptide complex to the nucleus of a cell. In some embodiments, the alpha-helical linker comprises a nucleotide encoding the sequence of (A(EAAAK)$_3$A) (SEQ ID NO: 9). In some embodiments, the flexible linker comprises a nucleotide encoding the sequence of ((GGGGS)$_3$)(SEQ ID NO: 10). In some embodiments, the alpha-helical linker is attached to the amino-terminal end of a nuclear localization signal (NLS). In some embodiments, the NLS is myc (PAAKRVKLD) (SEQ ID NO: 11). In some embodiments, the NLS is SV40 (AVKRPAATKKAGQAKKKKLD) (SEQ ID NO: 12).

As noted herein, the second promoter of the nucleic acid molecule is operably connected to a guide RNA (gRNA). In some embodiments of the nucleic acid molecule, the second promoter is an RNA polymerase II promoter of about 150-250 nucleotides (base pairs) in length.

As will be recognized by the skilled artisan, guide-RNA (gRNA) is a guide-polynucleotide including ribonucleotides and at least a guide-sequence that is able to hybridize with a target-polynucleotide and is able to direct sequence-specific binding of the RNA-guided nuclease system to a target-polynucleotide. In this regard, gRNA can be described as a fusion of sequences, including a sequence for Cas polypeptide binding, which can be referred to as a gRNA scaffold sequence, and a sequence for directing a Cas-gRNA complex to a target DNA, which can be referred to as a gRNA targeting sequence.

Some embodiments of the nucleic acid molecule further include a polyA domain. In some embodiments, the poly A domain is an SV40 polyA domain. In some embodiments, the poly A domain is about 115 to about 130 nucleotides (base pairs) in length.

The presently-disclosed subject matter further includes a vector comprising a nucleic acid as disclosed herein. In some embodiments, the vector is an adeno-associated virus (AAV) vector.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

In certain instances, nucleotides and polypeptides disclosed herein are included in publicly-available databases, such as GENBANK® and SWISSPROT. Information including sequences and other information related to such nucleotides and polypeptides included in such publicly-available databases are expressly incorporated by reference. Unless otherwise indicated or apparent the references to such publicly-available databases are references to the most recent version of the database as of the filing date of this Application.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, in some embodiments ±0.1%, in some embodiments ±0.01%, and in some embodiments ±0.001% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter is further illustrated by the following specific but non-limiting examples. The following examples may include compilations of data that are representative of data gathered at various times during the course of development and experimentation related to the present invention.

EXAMPLES

The use of CRISPRi to decrease targeted gene expression for clinical applications has been inhibited by delivery challenges. Existing constructs are too large to fit within the 4.7 kb packaging size limitation of adeno-associated virus (AAV), the only FDA approved viral vector for clinical use. The present invention beneficially provides nucleotides including CRISPRi components designed to generate a single AAV vector that contains all functional elements and effectively knocks down gene expression. These Examples describe exemplary studies related to the present invention. First, nuclear targeting of *Staphylococcus aureus* deactivated Cas9 (SadCas9) was increased 4-fold by using a helical linker and the c-Myc nuclear localization signal. Second, an amino-terminal Krüppel associated box (KRAB) construct was identified as the most effective in decreasing expression of target genes in vitro. Third, promoters were designed for guide RNA and mini-promoters were evaluated for expression of KRAB-SadCas9 in liver cells. The final construct decreased protein convertase subtilisin/kexin type 9 (Pcsk9) mRNA and secreted protein 5-fold in vitro. The corresponding AAV2/8 vector was localized in nuclei of liver cells and decreased Pcsk9 mRNA and serum protein levels by 30% in vivo. This single AAV approach provides a potential clinically translatable method for decreasing targeted gene transcription by CRISPRi in vivo.

Example 1: Plasmid Construction

Plasmids were created with combinations of DNA digests (NEB enzymes, New England Biolabs, Ipswich, Mass., USA), synthetic DNA from either IDT (Integrated DNA Technologies, Coralville, Iowa, USA) or Genewiz (South Plainfield, N.J., USA), and PCR with Q5 polymerase (NEB). DNA was sequenced at Genewiz. The AAV2 backbone plasmid was purchased from Cell Biolabs (San Diego, Calif.; #VPK-410). The ZsGreen plasmid was purchased from Takara Bio (Mountain View, Calif.; #632428) and PCR was used to remove the DR degradation domain. Plasmids obtained from Addgene include Sleeping Beauty SBtet-Neo (#60509)[11] and SB100X expression (#34879).[10] A humanized form of SadCas9 was obtained from plasmid #70703[19] and the Kpn1/Pci1 fragment containing U6:sgRNA and Bsal(-) AmpR was obtained from plasmid #84040[20]. All relevant SB and AAV plasmids will be available at Addgene.

Example 2: gRNA Sequences

The published gRNA sequence of mouse Pcsk9 referred to as gRNA2 was used, 4 which is 5'-GAGGGAAGGGA-TACAGGCTGGA-3' (SEQ ID NO: 16). For human VIMENTIN, the sequence of gRNA C5 is 5'-ACGAA CGAGGGCGCGGTGGGT-3' (SEQ ID NO: 17). The 5' "A" was changed from the genomic "G" to decrease the hairpin melting temperature. Both "A" and "G" are efficient U6 and 7SK transcription start sites. 21 The gStop sequence is 5'-GGAGACCAAG-GCAGTTTTTT-3' (SEQ ID NO: 18). The gRNA present in many vector backbones is referred to here as non-targeting (NT); 5'-GGAGAC-CACGGCAGGTC-TCA-3' (SEQ ID NO: 19).

Example 3: Cells

Cell lines purchased from ATCC (Manassas, Va., USA) included human ARPE-19 (ATCC #CRL-2302) and mouse AML-12 (ATCC #CRL-2254). Both lines were grown in complete media consisting of DMEM/F12 (Thermo Fisher Scientific, Waltham, Mass., USA; GIBCO #10565-018) supplemented with 15 mM HEPES (GIBCO #15630080) and 10% (v/v) fetal bovine serum (GIBCO #26140-079). Confluent cultures were treated with TrypLE Express (GIBCO #12604) to passage cells.

Example 4: Generation of Cell Lines

Cells at 50%-75% confluence in 6-well plastic plates were co-transfected with 1 mg each of SB SadCas9 and SB100X expression plasmids along with 8 mL FuGENE HD (Promega, Madison, Wis., USA; #E2311). The transfection reagents were prepared in serum-free medium at a final volume of 200 mL and added to cells that were in 3 mL of complete media. After 2 days, media was replaced with fresh complete media containing G418 (Corning #30-234-CR) at either 1.0 mg/mL (AML-12 cells) or 1.5 mg/mL (ARPE-19). These concentrations provided 100% death of parental, non-transfected cells after 10-12 days of treatment.

Example 5: Mouse Pcsk9 ELISA

Levels of Pcsk9 protein were determined from cultures of AML-12 cells or mouse sera. AML-12 cells in serum-free media became somewhat non-adherent on plastic and non-adherent on glass. Therefore, AML-12 cells and polyclonal cell lines were added to 6-well plastic plates that were coated with Geltrex (GIBCO #A15696-01). Each well was incubated with 1.2 mL Geltrex for 2 h at room temperature (RT). Wells were washed with PBS immediately before plating cells in complete media. The following day, wells were washed and replaced with 3 mL of serum-free media containing 2 or 5 mg doxycycline/mL (Sigma-Aldrich, St. Louis Mo., USA; #D989) and incubated for 3 days. The lower concentration yielded similar results with less variability. For the experiments that compared CRISPRi activities of different promoters driving expression of KRAB-SadCas9 (e.g., CMV, Alb-AAT, or EF-1a), cells were not treated with doxycycline. Culture supernatant was collected, centrifuged at 17,000×g for 15 min at 4° C., diluted 1:5 in assay buffer, and subjected to a mouse Pcsk9 Quantikine ELISA (R&D Systems, Minneapolis, Minn., USA; catalog #MPC900). Values were normalized to levels of total RNA. Mouse sera were diluted 1:20 in PBS immediately after collection and another 1:5 in assay buffer before analysis.

Example 6: qPCR

RNA was isolated from cell lines and mouse livers. The procedure was identical for both sources except pieces of liver were placed directly into RNAprotect Tissue Reagent (QIAGEN GmbH, Hilden, Germany; #76106). Total RNA was isolated and separated from genomic DNA with an RNeasy Plus kit (QIAGEN #74124) according to the manufacturer's instructions. cDNA was prepared from 1 mg of RNA using an Applied Biosystems High Capacity cDNA Reverse Transcription kit (Thermo Fisher #4368814) according to the manufacturer's instructions. The same primers for mGAPDH and mPcsk9 were used as in Thakore et al.[4] Primers for humanized SadCas9 were F: 5'-CGCAT-AGAGGAAATT-ATAAGAACAACCGG-3' and R: 5'-TG AAGG-AATTGTCAAAGCTTACGGA-3'. qPCR of cDNA (2 mL) was performed with PerfeCTa SYBR Green FastMix ROX (Quanta-bio, Beverly, Mass., USA; #84071) using Applied Biosystems QuantStudio 3 PCR system. Amplification conditions were 95° C. for 10 min and 40 cycles of 95° C. for 15 s and 60° C. for 1 min. The Ct values of each target were normalized to Ct values of Gapdh to determine DCt, and fold-changes in target gene expression were calculated with the DDCt method.

Example 7: Antibodies

Mouse (#C15200230) and rabbit (#C15310260) antibodies against Sa Cas9 were purchased from Diagenode (Denville, N.J.). The rabbit antibodies were diluted 1:1,000 for blots, 1:2,000 for immunocytochemistry of cell lines, and 1:1,000 for liver sections. Secondary fluorescent antibodies were obtained from Thermo Fisher. The remaining antibodies were purchased from Cell Signaling Technologies (Danvers, Mass.).

Example 8: Immunoprecipitation

Cells in 10 cm plates were washed with PBS and then scraped and sonicated in 200 mL of PBS containing 2 Halt protease inhibitor (Thermo Scientific #78430). PBS-soluble protein was collected after a 17,000×g spin for 15 min at 4° C. Protein concentrations were determined with the Bicinchoninic acid (BCA) protein assay (Thermo Scientific) using BSA as the protein standard. For immunoprecipitations, 2 μL of 10% Triton X-100 in PBS (to decrease surface tension) and primary antibody was added to 200 j·tg of protein in a final volume of 200 μL. The antibodies included mouse anti-Sa Cas9 (1 j·tg) or mouse anti-FLAG (2 μL). After 1 hat RT, 10 μL of anti-mouse beads
(Cell Signaling Technologies, Danvers, Mass., USA; #5946) was added and incubated overnight at 4° C. with shaking. Beads were washed twice with 1 mL of PBS containing 0.1% Triton X-100, treated with 50 μL of 1×SDS sample buffer (Bio-Rad, Hercules, Calif., USA; #1610747) containing 2.5% 2-mercaptoethanol (Bio-Rad; #1610710), and heated at 70° C. for 10 min.

Example 9: Immunoblots

Proteins were electrophoresed in 4%-20% or 7.5% TGX gels (Bio-Rad) along with 5 μL or 10 μL, respectively, of SeeBlue Plus2 protein markers (Invitrogen/Thermo Fisher). Protein was transferred to 0.4 tm nitrocellulose membranes (Bio-Rad) in Tris/Glycine buffer without methanol at 100V for +120 mA (!15 min). Membranes were blocked with 2% BSA in TBS overnight at 4° C. Primary antibodies were incubated for 2 h at RT and secondary antibodies (alkaline phosphatase-conjugated, Jackson ImmunoResearch) for 1 h at RT. Blots were developed with NBT and BCIP (Pierce/Thermo Fisher).

Example 10: Immunocytochemistry

Cells were grown in 8-well Lab Tek II chamber slides (Thermo Fisher; #154941). Slides for AML-12 cells were pre-coated with 80 μL of Geltrex as described above (Mouse Pcsk9 ELISA). Cells were fixed for 15 min in formaldehyde solution (Sigma-Aldrich; #F1635) diluted 1:10 in PBS, washed with TBS, and then permeabilized with 0.25% Triton X-100 in TBS for 15 min. Non-specific sites were blocked overnight at 4° C. with TBS containing 2% immuno-globulin G (IgG)-free BSA (Jackson ImmunoResearch Laboratories, West Grove, Pa.; #001-000-161). Wells were incubated with primary and secondary antibodies diluted in TBS/1% IgG-free BSA. Fluorescent secondary antibodies were used at a dilution of 1:1,000. Cover-slips were mounted with ProLong Gold with 4',6-diamidino-2-phe-nylindole (DAPI) (Thermo Fisher; #P36941).

Example 11: AAV8 Mice Experiments

Plasmids were packaged in AAV8 particles and quantitated (vg/mL) at SignaGen Laboratories (Rockville, Md., USA). Quantitation was determined from qPCR of the SV40 pA. Male C57BL/6 mice were purchased from Jackson Laboratories (Bar Harbor, Me.). Mice at 6-8 weeks of age were anesthetized with 1.5% isoflurane and secured into a chamber exposing the tail. A single tail vein injection of 200 tL AAV solution ($5 \times 10^{10}$, $2 \times 10^{11}$, or $4 \times 10^{11}$ vg in PBS) or sterile PBS was administered using a 26G needle. 3 weeks later, mice were euthanized and blood was collected by cardiac puncture prior to collection of liver tissue that was stored in RNAprotect Tissue Reagent (QIAGEN). Whole blood was allowed to clot in Z tubes (Greiner Bio-one, Kremsmunster, Austria; #450470) by leaving it undisturbed at RT. The clot was removed by centrifuging at 1,000-2,000×g for 10 min in a refrigerated centrifuge. Approximately 100 tL of serum was collected per mouse and 10 tL immediately diluted 1:20 in PBS for the Pcsk9 ELISA. All procedures were performed in accordance with the VUMC Institutional Animal Care and Use Committee approved protocol and Association for Research in Vision and Ophthalmology guidelines.

Example 12: Immunohistochemistry

Frozen chunks of mouse liver were embedded in OCT and cryosectioned at a thickness of 7 microns. Slides were air-dried for 30 min at RT and stored at −80° C. Tissues were fixed and permeabilized as per the immunocytochemistry protocol (above) and blocked with 5% (v/v) normal donkey serum (NDS, Jackson ImmunoResearch; #017-000-121) in PBS for 1-3 days at 4° C. Sections were labeled with rabbit anti-Sa Cas9 (1:1,000 in 2% NDS) overnight at 4° C. Sections were washed with PBS and labeled with donkey anti-rabbit antibodies conjugated to Alexa 594 (1:200 in 1% NDS) and incubated for 2 h. Sections were washed twice with PBS, once with water, and air-dried. Coverslips were mounted with VECTASHIELD antifade mounting medium with DAPI (Vector Laboratories, Burlingame, Calif.; #H-1200).

Example 13: Design for SadCas9 Nuclear Targeting

Nuclear localization of SadCas9 was directly addressed using combinations of linkers and nuclear localization signals in the human retinal pigmented epithelium cell line, ARPE-19. The commonly used combination of a flexible 15 amino acid, glycine-rich (GR) linker and the SV40 nuclear localization signal (NLS) at the carboxyl-terminus of Sad-Cas9 resulted in only 6.7%±1.1% of transfected cells with nuclear SadCas9 (Table 1). However, a rigid helical 17 amino acid linker[7] before the c-Myc (myc) NLS increased nuclear localization of SadCas9 4-fold (27.0%±2.8%, p=0.0003). Therefore, the combination of a helical linker (EA linker) and myc NLS was used in all subsequent SadCas9 constructs.

The carboxyl-terminus of SadCas9 is juxtaposed against the topo-isomerase TOPO domain.[8] Since $Arg^{215}$ (circle above sequences in FIG. 1A) of SadCas9 interacts with the non-target strand proto-spacer adjacent motif (PAM),[8] an examination was conducted to determine whether truncations downstream of Are further enhanced the percentage of cells with nuclear SadCas9 while decreasing the size of SadCas9. Relative to wild-type (WT) SadCas9, removing 18 amino acids (D1036) decreased the percentage of cells with nuclear SadCas9 2-fold (p=0.008) whereas removing an additional 3 amino acids (D1033) did not affect trafficking (FIG. 1A). However, the loss of 21 amino acids (D1,033) resulted in decreased protein levels relative to WT SadCas9 (FIG. 1B). Notably, these cell lines were generated using a Sleeping Beauty transposon system9,10 and expression of SadCas9 was under the control of a Tet-ON promoter.[11] This allowed us to quickly survey a polyclonal population of cells with protein expression limited by the addition of doxycycline (Dox). WT SadCas9 was detected exclusively in nuclei of Dox-treated cells (FIG. 1C), but the pattern was more reminiscent of nucleoli than nucleoplasm. An evaluation was conducted to determine whether KRAB would alter the nuclear distribution of SadCas9.

TABLE 1

Effects of Linkers (GR or EA) and Nuclear Localization Signals (SV40 or myc) on the Distribution of SadCas9 in Transiently Transfected ARPE-19 Cells

| SadCas9 Construct[a] | % Nuclear[b] |
|---|---|
| SadCas9-SV40 | 5.1 ± 0.8 |
| SadCas9-GR-SV40 | 6.7 ± 1.1 |
| SadCas9-EA-SV40 | 9.6 ± 3.6 |
| SadCas9-myc | 7.9 ± 0.3 |

TABLE 1-continued

Effects of Linkers (GR or EA) and Nuclear Localization Signals (SV40 or myc) on the Distribution of SadCas9 in Transiently Transfected ARPE-19 Cells

| SadCas9 Construct[a] | % Nuclear[b] |
|---|---|
| SadCas9-GR-myc | 14.9 ± 1.2 |
| SadCas9-EA-myc | 27.0 ± 2.8[c] |

[a]Linker sequences of the 15-amino acid GR is [(GGGGS)3] and the 17-amino acid EA is [A(EAAAK)3A].
[b]Determined from dividing the number of cells with nuclear SadCas9 by the total number of immunolabeled cells. At least 250 cells were counted per experiment and the results are presented as the mean ± SD of three independent experiments.
[c]p = 0.0003 from one-way ANOVA followed by the Dunnett post-hoc multiple comparison test.

Example 14: KRAB Placement within SadCas9

Figure 2B:
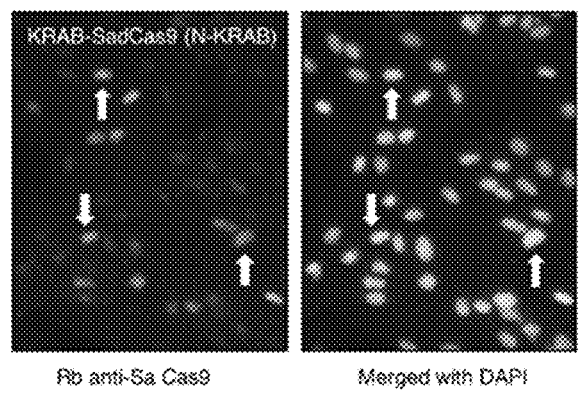
Figure 2C:
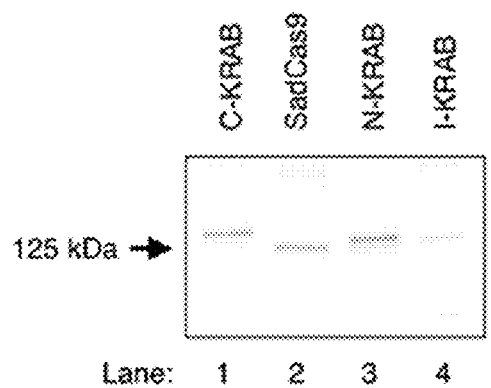

The accessibility of the SadCas9 amino-terminus was examined using antibody-antigen binding as a model for transcription factor protein-protein interactions. Either 1 amino acid (T) or the commonly used 7-amino acid flexible, GS linker (GGSGGGS) was used to separate the FLAG-tag from the amino-terminus of SadCas9. Co-labeling with antibodies against Cas9 (red) and FLAG (green) revealed increased availability of the amino-terminal "spatial domain" of SadCas9 with the GS linker (FIG. 2A). The GS linker was therefore included between KRAB and SadCas9 in the amino-terminal (N-KRAB) construct. Additional constructs with KRAB positioned at either an internal site (I-KRAB) or the carboxyl-terminus (C-KRAB) of Sad-Cas9 were used to generate cell lines. The cellular distribution of N-KRAB (FIG. 2B) and C-KRAB (data not shown) were exclusively nuclear, and importantly, consistent with a nucleoplasmic pattern in contrast to the nucleolar-like pattern of SadCas9 (FIG. 1C). These results establish that inclusion of KRAB changes the nuclear localization of SadCas9. In contrast, I-KRAB was below the level of detection in immunocytochemistry experiments. A comparison of expressed protein revealed similar levels of N-KRAB and C-KRAB, but dramatically lower levels of I-KRAB (FIG. 2C); I-KRAB was therefore not included in subsequent functional studies. The unexpected finding that N-KRAB migrated to a position between SadCas9 and C-KRAB (FIG. 2C) warranted further examination.

Example 15: Analysis of N-KRAB

Figure 3A:
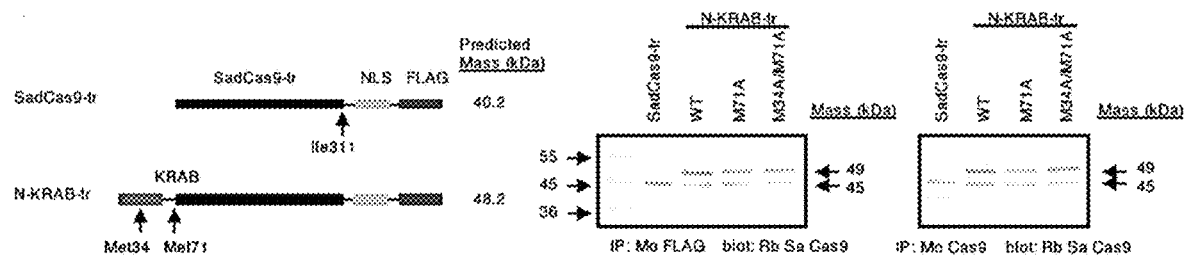
FIGS. 3A-3C. Analysis of N-KRAB constructs.
Figure 3B:
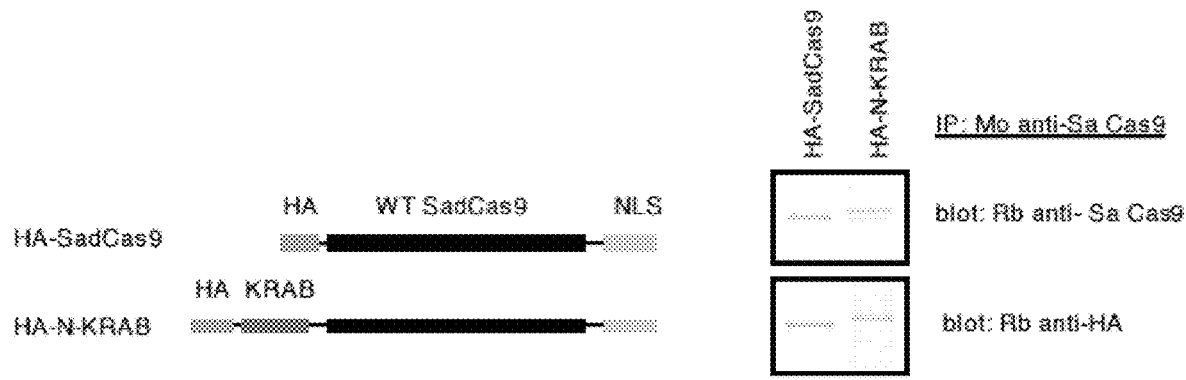
Figure 3C:
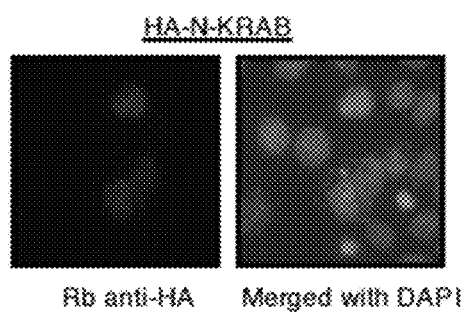

Experiments were performed to assess whether N-KRAB was being translated at a downstream methionine, the KRAB domain was being cleaved, or alternatively, N-KRAB displayed an anomalous migration pattern (FIG. 3). Potential downstream translation start sites were evaluated with SadCas9 constructs that were truncated (-tr) at Ile$^{311}$ to provide accurate determination of mass on blots (FIG. 3A). The constructs had FLAG-tags at the carboxyl-terminus to allow detection of the Cas9 proteins with antibodies against FLAG, as well as Sa Cas9. N-KRAB-tr is predicted to be 8 kDa larger than Sad-Cas9-tr but the results from blots document a 4 kDa difference. Mutation of Met$^{34}$ within KRAB and Met$^{71}$ at the beginning of SadCas9 (M34A/M71A) did not result in an increased size (FIG. 3A), establishing that translation is not occurring at a downstream site. The possibility that N-KRAB is cleaved within the KRAB domain was examined with a hemagglutinin (HA)-tag at the amino-terminus of full-length SadCas9 (HA-SadCas9) and N-KRAB (HA-N-KRAB; FIG. 3B). Mouse anti-Cas9 immunoprecipitates from transiently transfected cells were probed with rabbit antibodies against Cas9 (top panel) or HA-tag (bottom panel). A larger apparent mass of HA-N-KRAB relative to HA-SadCas9 was observed with both antibodies, which is consistent with an intact KRAB domain, at least within a subpopulation of HA-N-KRAB molecules. Finally, transfected cells labeled with anti-HA (FIG. 3C) confirm that a population of full-length HA-N-KRAB molecules with a functional myc-NLS reaches the nucleus. Together, the results were consistent with an anomalous migration pattern of N-KRAB. N-KRAB and C-KRAB were examined in functional studies, where CRISPRi activity of N-KRAB constructs would establish that its unusual migration pattern in gels was not due to a loss of KRAB function.

Example 16: CRISPRi Activity Against VIMENTIN

Figure 4A:
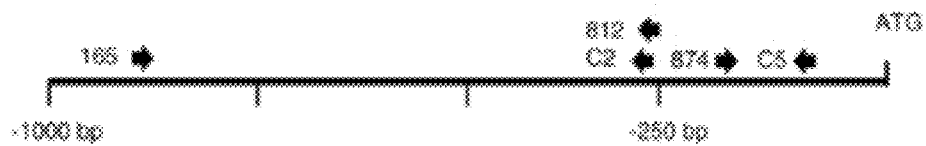
FIGS. 4A-4F. CRISPRi activity against the cytoskeletal protein vimentin.
Figure 4B:
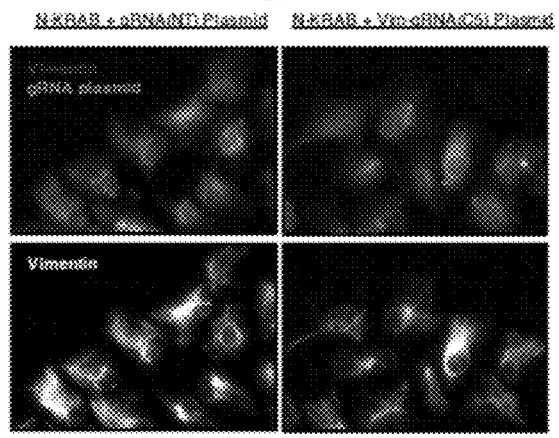
Figures 4C, 4D:
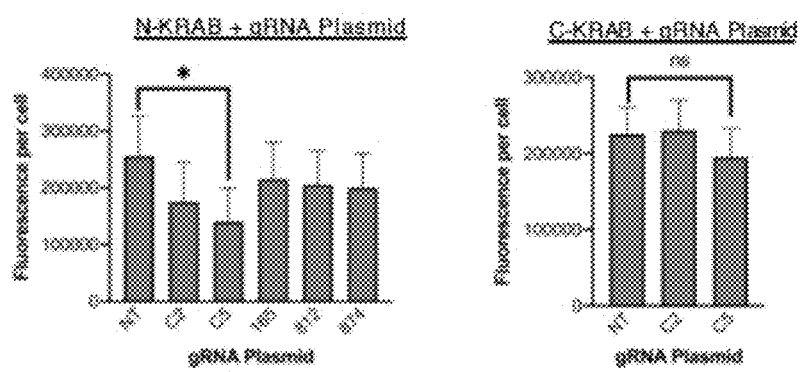
Figure 4E:
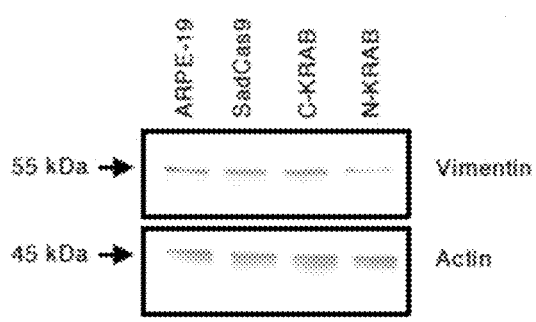
Figure 4F:
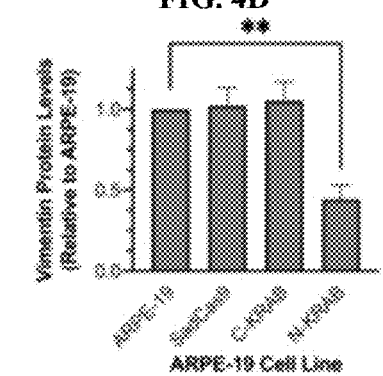

The ability of the SadCas9 constructs with KRAB to decrease gene expression was tested in ARPE-19 cell lines with VIMENTIN as the target. Polyclonal cell lines expressing N-KRAB or C-KRAB under control of the Tet-ON promoter were transiently transfected with a bicistronic plasmid composed of the SV40 promoter driving expression of ZsGreen and the U6 promoter driving expression of sgRNA (FIG. 4A) Example fluorescence images of N-KRAB cells expressing either non-targeting (NT) or VIMENTIN (C5) gRNA labeled with anti-vimentin are shown in FIG. 4B. Vimentin immunofluorescence intensity (red channel) was measured in ZsGreen-positive cells (green channel) with the application ImageJ. Red fluorescence was measured in at least 100 ZsGreen-positive cells and presented as the mean±SD of fluorescence per cell. An analysis of 5 vimentin gRNAs revealed that co-expression of the C5 gRNA plasmid resulted in a significant 2-fold decrease in vimentin immunofluorescence in the N-KRAB cell line (FIG. 4C; p=0.02) relative to the NT gRNA. However, there was no significant difference with the C-KRAB cell line expressing the same C5 gRNA (FIG. 4D). Bicistronic plasmids with the 7SK promoter provided identical results as the U6 promoter.[1] Therefore, additional cell lines were generated with either SadCas9, N-KRAB, or C-KRAB together with the 7SK promoter driving expression of the vimentin C5 gRNA. Examination of immunoreactive vimentin from the SDS-soluble fraction of each cell line (FIG. 4E) revealed that only the N-KRAB cell line decreased vimentin protein levels 2-fold (FIG. 4F; p=0.0004). These results show that N-KRAB was a more effective CRISPRi construct than C-KRAB against VIMENTIN.

Example 17: CRISPRi Activity Against Pcsk9

Figure 5A:
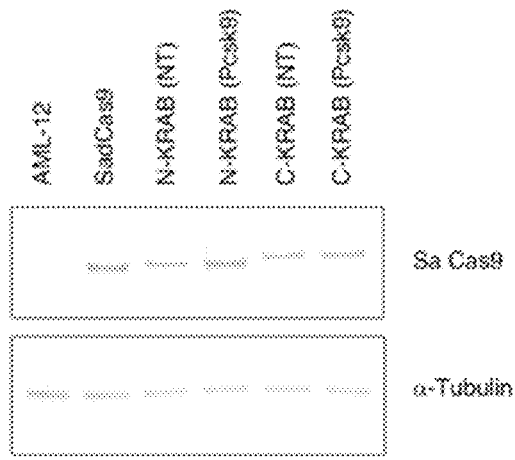
FIGS. 5A-5C. CRISPRi Activity Against the Secreted Protein Pcsk9.
Figure 5B:
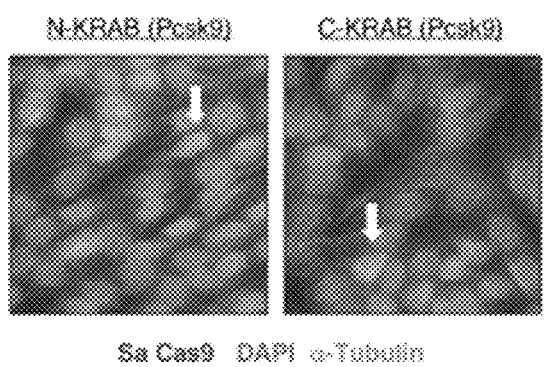
Figure 5C:
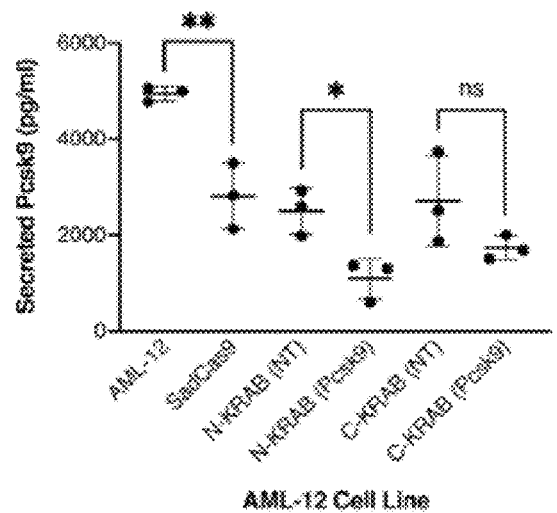

The dual AAV system has been shown to decrease levels of serum Pcsk in vivo.[4] The CRISPRi activities of N-KRAB and C-KRAB were evaluated using the same gRNA (gRNA2).[4] Tet-ON plasmids with the U6 promoter driving expression of non-targeting (NT) or Pcsk9 gRNA were stably expressed in mouse liver AML-12 cells and treated with 5 jig Dox/mL of serum-free media. Similar levels of SadCas9 proteins were detected on blots from cell extracts (FIG. 5A) and exclusive nuclear labeling (FIG. 5B) was detected in the cell lines that express N-KRAB (left panel) or C-KRAB (right panel) along with Pcsk9 gRNA. However, SadCas9 displayed the same punctate, nucleolar-like labeling (data not shown) as in the ARPE-19 cell lines (FIG. 1C). Supernatant from cells grown in 5 jig Dox/mL of serum-free media were subjected to a Pcsk9 ELISA. Cells expressing SadCas9 alone showed a significant (p=0.006) 2-fold reduction in secreted Pcsk9 levels relative to parental AML-12 cells (FIG. 5C). A similar reduction was observed for N-KRAB(NT) or C-KRAB(NT). A further 3-fold and 1.5-fold reduction in secreted Pcsk9 was observed for N-KRAB(Pcsk9) and C-KRAB(Pcsk9) but only N-KRAB (Pcsk9) was significant (p=0.02). However, the CRISPRi activity of C-KRAB(Pcsk9) was close to being significant (p=0.06) when compared to SadCas9. Nonetheless, since N-KRAB decreased expression of both Pcsk9 and vimentin, N-KRAB was chosen as the model CRISPRi construct.

Example 18: Analysis of U6 and 7SK Promoters

Figure 6A:
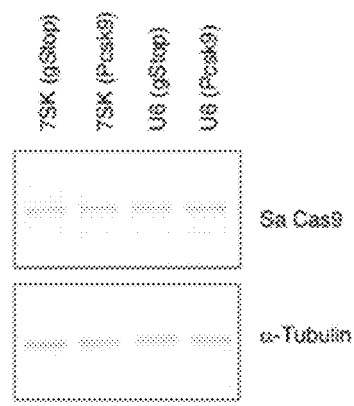
FIGS. 6A-6D. Comparison of 7SK and U6 Promoters Driving Expression of gRNA. AML-12 cell lines expressing N-KRAB and either 7SK or U6 promoters were treated with 2 jig Dox/mL for 3 days.
Figure 6B:
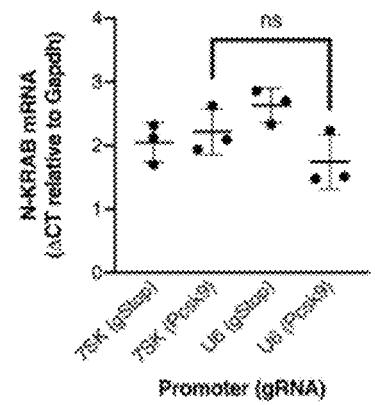
Figure 6C:
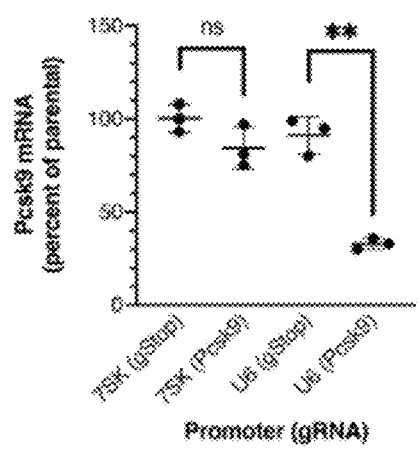
Figure 6D:
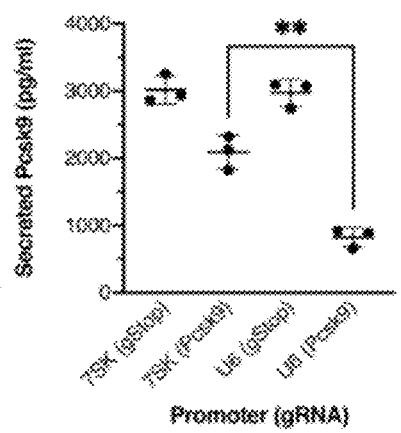

Whereas no differences between the U6 and 7SK promoter were detected for the vimentin experiments with ARPE-19 cells, a significant difference was observed from AML-12 cell lines. For these experiments, the negative control was a gStop gRNA composed of 6-"T" s, which effectively terminates transcription of both promoters.[12] Thus, these experiments could be considered as plus or minus guide RNA with the only other difference being the U6 or 7SK promoter. Cells were treated with 2 jig Dox/mL of serum-free media for 3 days. The cell lines expressed similar levels of N-KRAB protein (FIG. 6A) and mRNA (FIG. 6B). The U6(Pcsk9) construct decreased Pcsk9 mRNA 3-fold (FIG. 6C; p=0.0006) and secreted Pcsk9 3.5-fold (FIG. 6D; p=0.0001) relative to the U6(gStop) construct. In contrast, the 7SK(Pcsk9) construct did not significantly decrease Pcsk9 mRNA (FIG. 6C), but significantly decreased secreted Pcsk9 1.5-fold (FIG. 6D; p=0.008) relative to 7SK(gStop). Since the U6 promoter displayed a 2.5-fold decrease in secreted Pcsk9 relative to the 7SK promoter (FIG. 6D, p=0.002), the U6 promoter was used in subsequent CRISPRi constructs.

Example 19: Analysis of Promoters for N-KRAB

Figure 7A:
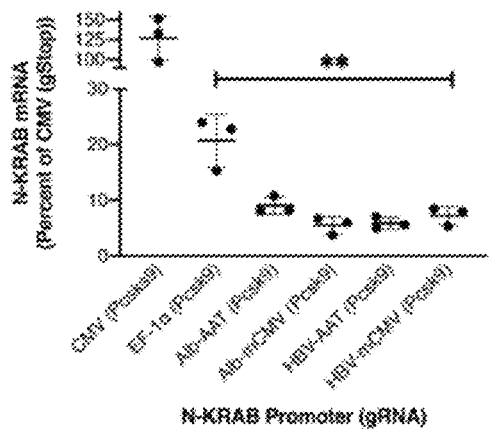
FIGS. 7A-7C. Comparison of Promoters Driving Expression of KRAB-SadCas9 (N-KRAB).
Figure 7B:
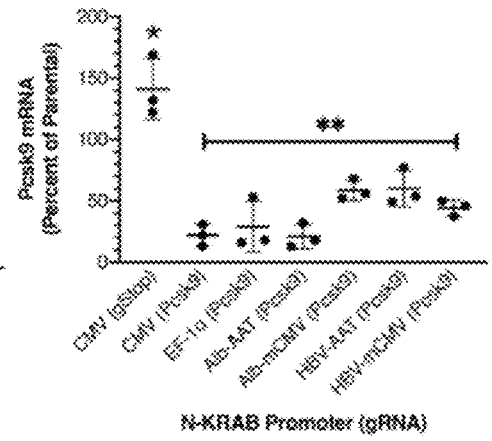
Figure 7C:
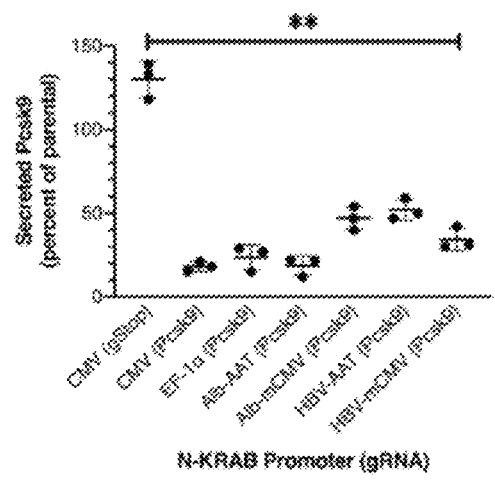
Figure 8A:
FIGS. 8A-8E. Analysis of a Single AAV CRISPRi that Targets Pcsk9 in Mice.

The remaining element for the design of the AAV plasmid was the promoter to drive expression of N-KRAB. For these experiments in AML-12 cell lines, the TET-On promoter was replaced with the general EF-1α promoter or more hepatocyte-specific combinations of enhancers and promoters.[13] The size of the enhancers and promoters used for these studies is shown in Table 2. Importantly, these plasmids contain all functional CRISPRi components and are within the size limitation of AAV packaging. Although inclusion of the CMV promoter exceeds the 4.7 kb AAV limit, it was used with gRNA for Pcsk9 or gStop as the positive and negative controls, respectively. The results showed that all tested promoters displayed 5- to 16-fold lower levels of N-KRAB mRNA relative to CMV (FIG. 7A). However, the EF-1α and the albumin enhancer/rz1-antitrypsin (Alb-AAT) promoters were as effective as CMV in decreasing levels of Pcsk9 mRNA (5-fold, FIG. 7B) and secreted protein (5-fold, FIG. 7C). A diagram of the elements used to generate the 4.7 kb (including ITRs) AAV plasmids is shown in FIG. 8A.

TABLE 2

Enhancers and Promoters Used to Express KRAB-SadCas9 (N-KRAB)

| Name | Abbreviation | Size (bp) | Function |
|---|---|---|---|
| Individual Components | | | |
| Albumin | Alb | 205 | enhancer |
| Hepatitis B enhancer II | HBV | 155 | enhancer |
| a1-antitrypsin | AAT | 162 | promoter |
| mini CMV | mCMV | 59 | promoter |
| Combined Enhancer and Promoters | | | |
| Elongation factor 1a | EF-1a | 271[a] | |
| | Alb-AAT | 367[a] | |
| | Alb-mCMV | 370[a] | |
| | HBV-AAT | 332[a] | |
| | HBV-mCMV | 285[a] | |

[a]Size of Mlu1/EcoR1 insert in Sleeping Beauty and AAV plasmids.

Example 20: In Vivo Efficacy of AAV8.Pcsk9CRISPRi

Figure 8B:
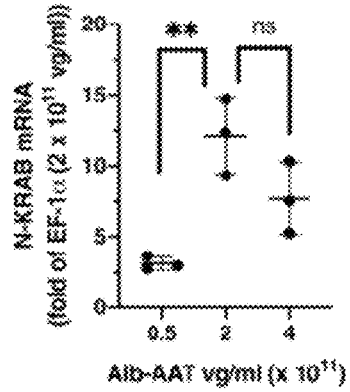
Figure 8C:
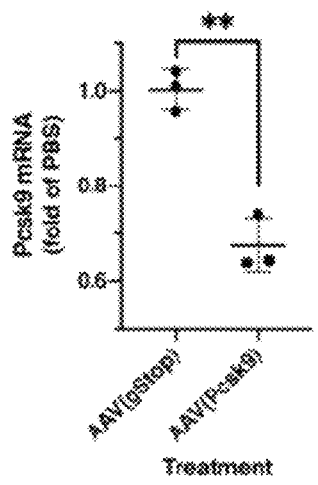
Figure 8D:
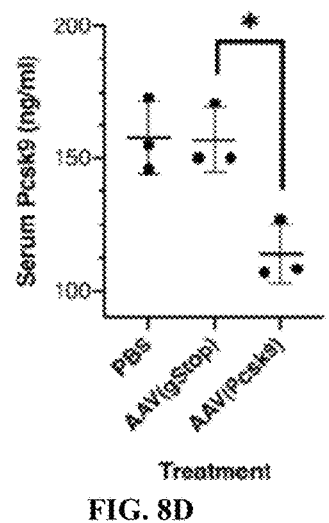
Figure 8E:
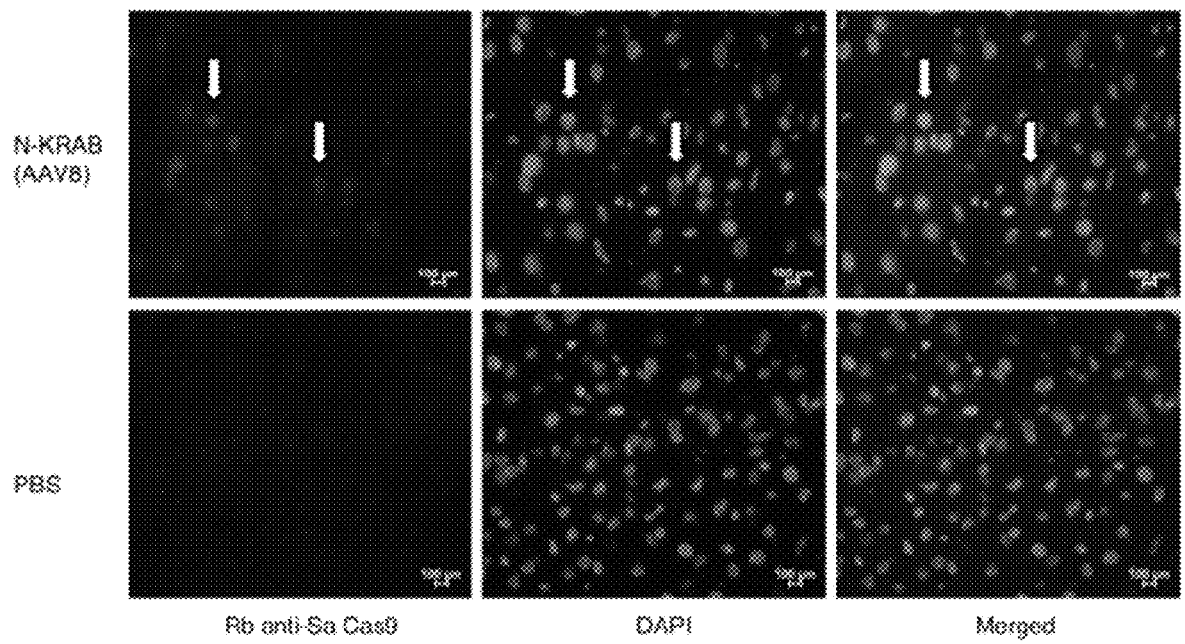

Male mice were injected into the tail vein with AAV2/8 viruses and sacrificed 3 weeks later. RNA from liver was used to measure levels of N-KRAB and Pcsk9 mRNA and serum was collected to measure levels of Pcsk9 protein. Viruses with either the EF-1α or Alb-AAT promoter along with Pcsk9 gRNA were evaluated for levels of N-KRAB mRNA from livers (FIG. 8B). At doses of 2×1011 vg/mouse, the iCt values obtained from the Alb-AAT promoter virus corresponded to 12.1±2.7-fold higher levels of N-KRAB mRNA relative to the EF-1α promoter virus (p<0.0001). A 4-fold decrease in the dose of the Alb-AAT promoter virus to 5×1010 vg/mouse resulted in a similar 3.9-fold lower level of N-KRAB mRNA (p=0.006). In contrast, a 2-fold increase to 4×1011 vg/mouse resulted in a trend toward lower levels of N-KRAB mRNA. The functional effects of AAV8 Alb-AAT viruses were evaluated with either Pcsk9 or gStop gRNA at a dose of 2×1011 vg/mouse. An analysis of Pcsk9 mRNA from livers revealed that the Pcsk9 gRNA produced a 32% decrease in Pcsk9 mRNA relative to the virus with the gStop gRNA (FIG. 8C; p=0.0014). Similarly, the virus with Pcsk9 gRNA reduced levels of serum Pcsk9 protein 27% relative to the virus with gStop gRNA (FIG. 8D; p=0.013). Finally, immunoreactive N-KRAB in liver sections prepared from mice injected with either virus (FIG. 8E, top panels) or PBS (bottom panels) were examined. Virally transduced livers displayed predominant nuclear labeling of N-KRAB that was above the level of control livers.

Discussion of Examples 13-20

Targeting of CRISPR constructs to the nucleus has historically utilized one[14,15] or two[4] copies of the SV40 nuclear localization signal (NLS) along with an additional nucleoplasm-targeting sequence.[4,15] The lack of reports that document functionality of these targeting sequences is surprising. The effectiveness of NLS-targeting was evaluated with a single SV40 or c-Myc NLS. A single c-Myc NLS, along with a critical helical peptide, provide efficient nuclear localization of the N-KRAB CRISPRi construct both in vitro and in vivo.

The finding that SadCas9 localizes to nucleolar-like structures in two different cell types was unexpected. Interestingly, SadCas9 has two potential nucleolar localization motifs within the bridge-helix domain. The first motif 51-KRxxxRxxRxR-61 has homology with Influenza A virus nonstructural protein 1 (NS1A)[16] and the second motif 55-RR(I/L)xxxR-61 has homology with a subnuclear targeting arginine domain (STAD).[17] However, K51A/R52A/R55A/R56A mutations did not alter the nuclear pattern of SadCas9 immunoreactivity (data not shown). It was contemplated that co-expression of sgRNA within the same plasmid as SadCas9 would alter the distribution of SadCas9 to a nucleoplasmic location. Inclusion of the prototypic non-targeting (NT) gRNA found in most Cas9 plasmids did not alter the distribution of SadCas9 in ARPE cell lines (data not shown). This provides a cautionary note for *S. aureus* Cas9 CRISPR editing of nucleoplasmic genes as proper localization would likely result in efficient gene editing. It is possible that other gRNAs would provide nucleoplasmic localization or Cas9 is trafficked differently than catalytically inactive dCas9. Further investigation is clearly required to establish the mechanism of SadCas9 nucleolar-like localization. Fortunately, inclusion of KRAB at either the amino- or carboxyl-terminus of SadCas9 resulted in nucleoplasmic localization of the CRISPRi constructs.

The position of KRAB within SadCas9 was examined in three locations. Addition of KRAB at an internal site between $Glu^{277}$ and $Leu^{297}$, a region that lacks contact points with sgRNA,[8] resulted in low protein levels, which is likely due to protein instability. Therefore, constructs with KRAB at either the amino-terminus (N-KRAB) or carboxyl-terminus (C-KRAB) of SadCas9 were focused upon. The N-KRAB construct was more effective than C-KRAB at decreasing levels of both vimentin and Pcsk9. Thus, N-KRAB was chosen as the model CRISPRi construct.

Both U6 and 7SK RNA promoters have been used to express sgRNA. Both promoters provided similar results against VIMEN-TIN in human ARPE cells, however, there was a clear difference against Pcsk9 in mouse AML-12 cells. This difference may be due to human versus mouse cells or cell types. Nonetheless, the U6 promoter appears to be an overall better choice for expression of sgRNA.

The biggest constraint for including all CRISPRi components into the 4.7 kb packaging limitation of AAV is the size of a promoter driving expression of N-KRAB. Based on the current results, the maximum size of the promoter is 370 bp. Mouse liver cell lines were used to compare the efficacy of several enhancer/promoters that are within this size constraint. The 675 bp hepatocyte-selective combination of the albumin-enhancer and a1-antitrypsin promoter (Ealb-Pa1AT)[13] was reduced in size to 370 bp (Alb-AAT). The 205 bp Alb enhancer contains the functional elements of the larger 370 bp enhancer, whereas the 162 bp AAT promoter lacks the upstream AP-1 and C/EBP elements but contains the tissue-specific and downstream elements of the larger 305 bp promoter. The smaller Alb-AAT enhancer/promoter is likely less active than the larger Ealb-Pa1AT construct that displayed only 2-fold less luciferase activity relative to CMV from liver extracts.[13] The Alb-AAT and EF-1a promoters produced 14-fold and 6-fold lower levels of N-KRAB mRNA, respectively, relative to CMV. However, the Alb-AAT and EF-1a promoters each produced a similar 5-fold decrease in Pcsk9 mRNA and secreted Pcsk9 as cells with the CMV promoter. These results establish that the Alb-AAT enhancer/promoter produced levels of N-KRAB that was sufficient for a maximal CRISPRi response in these cells.

AAV plasmids were packaged in AAV8 vectors to examine CRISPRi function in mouse livers. The first set of experiments were designed to compare doses of viruses to the levels of N-KRAB mRNA from livers. Mice were sacrificed 3 weeks after the injection, a time point with maximal reduction of serum Pcsk9 with the dual AAV system.[4] The results of these studies suggest that a dose of $2\times10^{11}$ vg/mouse produced maximal or near-maximal levels of N-KRAB mRNA at the 3-week time point. At this dose, the Alb-AAT promoter generated 12-fold higher levels of N-KRAB mRNA relative to the EF-1A promoter, establishing that the Alb-AAT promoter is significantly more efficacious than the EF-1a promoter in mouse livers.

The final experiments addressed levels of Pcsk9 mRNA from mouse livers and protein from sera. Mice were tail-injected with PBS or $2\times10^{11}$ vg/mouse of AAV2/8 containing Alb-AAT with either gStop or Pcsk9 gRNA. Relative to the AAV.gStop virus, the AAV.Pcsk9 virus decreased levels of mRNA 32% and protein 27%. This is less than the 50% and 83% reductions in mRNA and protein, respectively with the dual AAV system.[4] It should be noted that those experiments involved a 12 h fasting period before analysis. Glucagon signaling, which is elevated in fasting, has been shown to increase Pcsk9 protein turnover without affecting mRNA levels,[18] which may in part explain the difference in mRNA and protein levels that were obtained between the two studies. Nonetheless, liver cell lines with identical CRISPRi components as the AAV produced 80% reductions in both mRNA and protein. The enhancer/promoter elements could be further optimized for increased expression in vivo. However, the results clearly establish that a functional CRISPRi construct that decreases expression of an endogenous gene can be packaged in a single AAV. This will increase the efficacy of targeting clinically relevant genes, particularly in post-mitotic cells such as neurons (for review see Li and Samulski[5]).

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Bellefroid, E. J., Poncelet, D. A., Lecocq, P. J., Revelant, O., and Martial, J. A. (1991). The evolutionarily conserved Krüppel-associated box domain defines a subfamily of eukaryotic multifingered proteins. Proc. Natl. Acad. Sci. USA 88, 3608-3612.
2. Margolin, J. F., Friedman, J. R., Meyer, W. K.-H., Vissing, H., Thiesen, H.-J., and Rauscher, F. J., 3rd (1994). Krüppel-associated boxes are potent transcriptional repression domains. Proc. Natl. Acad. Sci. USA 91, 4509-4513.
3. Witzgall, R., O'Leary, E., Leaf, A., Önaldi, D., and Bonventre, J. V. (1994). The Krüppel-associated box-A (KRAB-A) domain of zinc finger proteins mediates transcriptional repression. Proc. Natl. Acad. Sci. USA 91, 4514-4518.
4. Thakore, P. I., Kwon, J. B., Nelson, C. E., Rouse, D. C., Gemberling, M. P., Oliver, M. L., and Gersbach, C. A. (2018). RNA-guided transcriptional silencing in vivo with *S. aureus* CRISPR-Cas9 repressors. Nat. Commun. 9, 1674-1682.
5. Li, C., and Samulski, R. J. (2020). Engineering adeno-associated virus vectors for gene therapy. Nat. Rev. Genet. 21, 255-272.

6. Lau, C.-H., Ho, J. W.-T., Lo, P. K., and Tin, C. (2019). Targeted transgene activation in the brain tissue by systemic delivery of engineered AAV1 expressing CRISPRa. Mol. Ther. Nucleic Acids 16, 637-649.
7. Marqusee, S., and Baldwin, R. L. (1987). Helix stabilization by Glu⁻ . . . Lys⁺ salt bridges in short peptides of de novo design. Proc. Natl. Acad. Sci. USA 84, 8898-8902.
8. Nishimasu, H., Cong, L., Yan, W. X., Ran, F. A., Zetsche, B., Li, Y., Kurabayashi, A., Ishitani, R., Zhang, F., and Nureki, O. (2015). Crystal structure of *Staphylococcus aureus* Cas9. Cell 162, 1113-1126.
9. Ivies, Z., Hackett, P. B., Plasterk, R. H., and Izsvák, Z. (1997). Molecular reconstruction of Sleeping Beauty, a Tc1-like transposon from fish, and its transposition in human cells. Cell 91, 501-510.
10. Mates, L., Chuah, M. K., Belay, E., Jerchow, B., Manoj, N., Acosta-Sanchez, A., Grzela, D. P., Schmitt, A., Becker, K., Matrai, J., et al. (2009). Molecular evolution of a novel hyperactive Sleeping Beauty transposase enables robust stable gene transfer in vertebrates. Nat. Genet. 41, 753-761.
11. Kowarz, E., Löscher, D., and Marschalek, R. (2015). Optimized Sleeping Beauty trans-posons rapidly generate stable transgenic cell lines. Biotechnol. J. 10, 647-653.
12. Gao, Z., Herrera-Carrillo, E., and Berkhout, B. (2018). Delineation of the exact transcription termination signal for type 3 polymerase III. Mol. Ther. Nucleic Acids 10, 36-44.
13. Kramer, M. G., Barajas, M., Razquin, N., Berraondo, P., Rodrigo, M., Wu, C., Qian, C., Fortes, P., and Prieto, J. (2003). In vitro and in vivo comparative study of chimeric liver-specific promoters. Mol. Ther. 7, 375-385.
14. Kleinstiver, B. P., Prew, M. S., Tsai, S. Q., Topkar, V. V., Nguyen, N. T., Zheng, Z., Gonzales, A. P., Li, Z., Peterson, R. T., Yeh, J. R., Aryee, M. J., et al. (2015). Engineered CRISPR-Cas9 nucleases with altered PAM specificities. Nature 523, 481-485.
15. Ran, F. A., Cong, L., Yan, W. X., Scott, D. A., Gootenberg, J. S., Kriz, A. J., Zetsche, B., Shalem, O., Wu, X., Makarova, K. S., et al. (2015). In vivo genome editing using *Staphylococcus aureus* Cas9. Nature 520, 186-191.
16. Melén, K., Kinnunen, L., Fagerlund, R., Ikonen, N., Twu, K. Y., Krug, R. M., and Julkunen, I. (2007). Nuclear and nucleolar targeting of influenza A virus NS1 protein: striking differences between different virus subtypes. J. Virol. 81, 5995-6006.
17. Mekhail, K., Rivero-Lopez, L., Al-Masri, A., Brandon, C., Khacho, M., and Lee, S. (2007). Identification of a common subnuclear localization signal. Mol. Biol. Cell 18, 3966-3977.
18. Spolitu, S., Okamoto, H., Dai, W., Zadroga, J. A., Wittchen, E. S., Gromada, J., and Ozcan, L. (2019). Hepatic glucagon signaling regulates PCSK9 and low-density lipoprotein cholesterol. Circ. Res. 124, 38-51.
19. Kleinstiver, B. P., Prew, M. S., Tsai, S. Q., Nguyen, N. T., Topkar, V. V., Zheng, Z., and Joung, J. K. (2015). Broadening the targeting range of *Staphylococcus aureus* CRISPR-Cas9 by modifying PAM recognition. Nat. Biotechnol. 33, 1293-1298.
20. Ye, L., Wang, J., Tan, Y., Beyer, A. I., Xie, F., Muench, M. O., and Kan, Y. W. (2016). Genome editing using CRISPR-Cas9 to create the HPFH genotype in HSPCs: An approach for treating sickle cell disease and b-thalassemia. Proc. Natl. Acad. Sci. USA 113, 10661-10665.
21. Gao, Z., Harwig, A., Berkhout, B., and Herrera-Carrillo, E. (2017). Mutation of nucleotides around the +1 position of type 3 polymerase III promoters: The effect on transcriptional activity and start site usage. Transcription 8, 275-287.
22. Boque-Sastre, R. et al. Head-to-head antisense transcription and R-loop formation promotes transcriptional activation. *Proc. Natl. Acad. Sci. USA* 112, 5785-5790 (2015).

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A nucleic acid, comprising:
   a) a nucleotide sequence encoding a Cas polypeptide that is a Cas9 polypeptide or a Cas12 polypeptide;
   b) a nucleotide sequence encoding a repressor domain or an activator domain attached to the nucleotide sequence encoding the Cas polypeptide via a nucleotide sequence encoding a first linker consisting of 6 to about 60 amino acids;
   c) a first promoter operably connected to the nucleotide sequence encoding the repressor or activator domain or the nucleotide sequence encoding the Cas polypeptide, such that the first promoter drives expression of the repressor or activator domain and the Cas polypeptide;
   d) a nucleotide sequence encoding a nuclear localization signal (NLS);
   e) a nucleotide sequence encoding a second linker, wherein the second linker is alpha-helical when the Cas polypeptide is the Cas9 polypeptide or flexible when the Cas polypeptide is the Cas12 polypeptide, and consists of about 15 to about 22 amino acids, wherein the second linker connects the Cas polypeptide to the NLS; and
   f) a second promoter operably connected to a nucleotide sequence encoding a guide RNA (gRNA).

2. The nucleic acid of claim 1, wherein the Cas polypeptide is a Cas9 polypeptide, and wherein the second linker is alpha-helical.

3. The nucleic acid of claim 2, wherein the Cas9 polypeptide is an SaCas9 polypeptide.

4. The nucleic acid of claim 2, wherein the Cas9 polypeptide comprises the amino acid sequence of SEQ ID NO: 1.

5. The nucleic acid of claim 2, wherein the Cas9 polypeptide comprises the amino acid sequence of SEQ ID NO: 3.

6. The nucleic acid of claim 1, wherein the Cas polypeptide is a Cas12 polypeptide, and wherein the second linker is flexible.

7. The nucleic acid of claim 1, wherein the repressor domain is selected from the group consisting of KRAB, SRDX, MAD1, and TIEG1.

8. The nucleic acid of claim 1, wherein the first linker attaches the nucleotide sequence encoding the repressor domain to the nucleotide sequence encoding the Cas polypeptide.

9. The nucleic acid of claim 8, wherein the first linker consists of about 7 amino acids.

10. The nucleic acid of claim 1, wherein the first promoter is an RNA polymerase II promoter of about 25 to about 400 nucleotides (base pairs) in length.

11. The nucleic acid of claim 10, wherein the first promoter is about 350 to about 375 nucleotides in length.

12. The nucleic acid of claim 1, wherein the second linker that is alpha-helical or flexible comprises a nucleotide sequence encoding the sequence of SEQ ID NO: 9, or SEQ ID NO: 10.

13. The nucleic acid of claim 1, wherein the NLS has a sequence selected from the group consisting of SEQ ID NO: 11 and SEQ ID NO: 12.

14. The nucleic acid of claim 1, and further comprising a polyA domain.

15. The nucleic acid of claim 1, wherein the nucleic acid is about 4600 to 4700 base pairs.

16. A vector comprising the nucleic acid of claim 1.

17. The vector of claim 16, wherein the vector is an adeno-associated virus (AAV) vector.

* * * * *

SEQUENCE LISTING

<160> NUMBER OF SEQ ID NOS: 19

<210> SEQ ID NO 1
<211> LENGTH: 32
<212> TYPE: PRT
<213> ORGANISM: Artificial Sequence
<220> FEATURE:
<223> OTHER INFORMATION: recombinant

<400> SEQUENCE: 1

Arg Ile Ile Lys Thr Ile Ala Ser Lys Thr Gln Ser Ile Lys Lys Tyr
1               5                   10                  15

Ser Thr Asp Ile Leu Gly Asn Leu Tyr Glu Val Lys Ser Lys Lys His
            20                  25                  30

<210> SEQ ID NO 2
<211> LENGTH: 96
<212> TYPE: DNA
<213> ORGANISM: Artificial Sequence
<220> FEATURE:
<223> OTHER INFORMATION: Recombinant

<400> SEQUENCE: 2
cgcatcatca agacaatcgc atctaaaact cagtcaataa aaaagtactc taccgatatc    60
ctggggaatc tctatgaagt gaagtcaaag aagcac    96

<210> SEQ ID NO 3
<211> LENGTH: 39
<212> TYPE: PRT
<213> ORGANISM: Artificial Sequence
<220> FEATURE:
<223> OTHER INFORMATION: Recombinant

<400> SEQUENCE: 3

Arg Ile Ile Lys Thr Ile Ala Ser Lys Thr Gln Ser Ile Lys Lys Tyr
1               5                   10                  15

Ser Thr Asp Ile Leu Gly Asn Leu Tyr Glu Val Lys Ser Lys Lys His
            20                  25                  30

Pro Gln Ile Ile Lys Lys Gly
        35

<210> SEQ ID NO 4
<211> LENGTH: 117
<212> TYPE: DNA
<213> ORGANISM: Artificial Sequence
<220> FEATURE:
<223> OTHER INFORMATION: recombinant

<400> SEQUENCE: 4
cgcatcatca agacaatcgc atctaaaact cagtcaataa aaaagtactc taccgatatc    60
ctggggaatc tctatgaagt gaagtcaaag aagcacccac aaatcattaa aaaaggt    117

<210> SEQ ID NO 5
<211> LENGTH: 32
<212> TYPE: PRT
<213> ORGANISM: Artificial Sequence
<220> FEATURE:
<223> OTHER INFORMATION: recombinant

<400> SEQUENCE: 5

Gly Lys Arg Asn Tyr Ile Leu Gly Leu Ala Ile Gly Ile Thr Ser Val
1               5                   10                  15

Gly Tyr Gly Ile Ile Asp Tyr Glu Thr Arg Asp Val Ile Asp Ala Gly
            20                  25                  30

<210> SEQ ID NO 6
<211> LENGTH: 96
<212> TYPE: DNA
<213> ORGANISM: Artificial Sequence
<220> FEATURE:
<223> OTHER INFORMATION: recombinant

<400> SEQUENCE: 6
ggcaaacgga actacatcct ggggcttgcc attgggataa ccagcgttgg ctacggaatt    60
attgattatg agacacgcga tgtgattgac gccggg    96

<210> SEQ ID NO 7
<211> LENGTH: 62
<212> TYPE: PRT
<213> ORGANISM: Artificial Sequence
<220> FEATURE:
<223> OTHER INFORMATION: recombinant

<400> SEQUENCE: 7

Arg Thr Leu Val Thr Phe Lys Asp Val Phe Val Asp Phe Thr Arg Glu
1               5                   10                  15

Glu Trp Lys Leu Leu Asp Thr Ala Gln Gln Ile Val Tyr Arg Asn Val
         20                  25                  30

Met Leu Glu Asn Tyr Lys Asn Leu Val Ser Leu Gly Tyr Gln Leu Thr
             35                  40                  45

Lys Pro Asp Val Ile Leu Arg Leu Glu Lys Gly Glu Glu Pro
     50                  55                  60

<210> SEQ ID NO 8
<211> LENGTH: 186
<212> TYPE: DNA
<213> ORGANISM: Artificial Sequence
<220> FEATURE:
<223> OTHER INFORMATION: recombinant

<400> SEQUENCE: 8
cggacactag tgaccttcaa ggatgtattt gtggacttca ccagggagga gtggaagctg    60
ctggacactg ctcagcagat cgtgtacaga aatgtgatgc tggagaacta taagaacctg   120
gtttccttgg ttatcagct tactaagcca gatgtgatcc tccggttgga gaagggagaa   180
gagccc                                                              186

<210> SEQ ID NO 9
<211> LENGTH: 17
<212> TYPE: PRT
<213> ORGANISM: Artificial Sequence
<220> FEATURE:
<223> OTHER INFORMATION: recombinant

<400> SEQUENCE: 9

Ala Glu Ala Ala Ala Lys Glu Ala Ala Ala Lys Glu Ala Ala Ala Lys
1               5                   10                  15

Ala

<210> SEQ ID NO 10
<211> LENGTH: 15
<212> TYPE: PRT
<213> ORGANISM: Artificial Sequence
<220> FEATURE:
<223> OTHER INFORMATION: recombinant

<400> SEQUENCE: 10

Gly Gly Gly Gly Ser Gly Gly Gly Gly Ser Gly Gly Gly Gly Ser
1               5                   10                  15

<210> SEQ ID NO 11
<211> LENGTH: 9
<212> TYPE: PRT
<213> ORGANISM: Artificial Sequence
<220> FEATURE:
<223> OTHER INFORMATION: recombinant

<400> SEQUENCE: 11

Pro Ala Ala Lys Arg Val Lys Leu Asp
1               5

<210> SEQ ID NO 12
<211> LENGTH: 20
<212> TYPE: PRT
<213> ORGANISM: Artificial Sequence
<220> FEATURE:
<223> OTHER INFORMATION: recombinant

<400> SEQUENCE: 12

```
Ala Val Lys Arg Pro Ala Ala Thr Lys Lys Ala Gly Gln Ala Lys Lys
1               5                   10                  15

Lys Lys Leu Asp
        20
```

<210> SEQ ID NO 13
<211> LENGTH: 381
<212> TYPE: DNA
<213> ORGANISM: Artificial Sequence
<220> FEATURE:
<223> OTHER INFORMATION: recombinant

<400> SEQUENCE: 13

| | | | | | |
|---|---|---|---|---|---|
| gcggccgcac | gcgtaaataa | cctgcgttat | agcatccact | cagtatccct | tgagcatgag | 60 |
| gtgacactac | ttaacatagg | gacgagatgg | tactttgtgt | ctcctgctct | gtcagcaggg | 120 |
| cactgtactt | gctgatacag | ggaatgtttg | ttcttaaata | ccatcattcc | ggacgtgttt | 180 |
| gccttggcag | tttccatgta | catgcagaaa | gaagtttgga | taggcgggcg | actcagatcc | 240 |
| cagccagtgg | acttagcccc | tgtttgctcc | tccgataact | ggggtgacct | tggttaatat | 300 |
| tcaccagcag | cctcccccgt | tgcccctctg | gatccactgc | ttaaatacgg | acgaggacag | 360 |
| ggccctgtct | cctcagaatt | c | | | | 381 |

<210> SEQ ID NO 14
<211> LENGTH: 285
<212> TYPE: DNA
<213> ORGANISM: Artificial Sequence
<220> FEATURE:
<223> OTHER INFORMATION: Recombinant

<400> SEQUENCE: 14

| | | | | | |
|---|---|---|---|---|---|
| gcggccgcac | gcgttcagtc | ctagtcgtga | ggctccggtg | cccgtcagtg | ggcagagcgc | 60 |
| acatcgccca | cagtccccga | gaagttgggg | ggaggggtcg | gcaattgaac | cggtgcctag | 120 |
| agaaggtggc | gcggggtaaa | ctgggaaagt | gatgtcgtgt | actggctccg | ccttttccc | 180 |
| gagggtgggg | gagaaccgta | tataagtgca | gtagtcgccg | tgaacgttct | ttttcgcaac | 240 |
| gggtttgccg | ccagaacaca | ggtgtcgtga | aaactacccg | aattc | | 285 |

<210> SEQ ID NO 15
<211> LENGTH: 4418
<212> TYPE: DNA
<213> ORGANISM: Artificial Sequence
<220> FEATURE:
<223> OTHER INFORMATION: recombinant

<400> SEQUENCE: 15

| | | | | | |
|---|---|---|---|---|---|
| gcggccgcac | gcgtaaataa | cctgcgttat | agcatccact | cagtatccct | tgagcatgag | 60 |
| gtgacactac | ttaacatagg | gacgagatgg | tactttgtgt | ctcctgctct | gtcagcaggg | 120 |
| cactgtactt | gctgatacag | ggaatgtttg | ttcttaaata | ccatcattcc | ggacgtgttt | 180 |
| gccttggcag | tttccatgta | catgcagaaa | gaagtttgga | taggcgggcg | actcagatcc | 240 |
| cagccagtgg | acttagcccc | tgtttgctcc | tccgataact | ggggtgacct | tggttaatat | 300 |
| tcaccagcag | cctcccccgt | tgcccctctg | gatccactgc | ttaaatacgg | acgaggacag | 360 |
| ggccctgtct | cctcagaatt | cgccaccatg | cggacactag | tgaccttcaa | ggatgtattt | 420 |
| gtggacttca | ccagggagga | gtggaagctg | ctggacactg | ctcagcagat | cgtgtacaga | 480 |
| aatgtgatgc | tggagaacta | taagaacctg | gtttccttgg | gttatcagct | tactaagcca | 540 |
| gatgtgatcc | tccggttgga | gaagggagaa | gagcccggcg | gttccggcgg | agggtccatg | 600 |

```
ggcaaacgga actacatcct ggggcttgcc attgggataa ccagcgttgg ctacggaatt      660
attgattatg agacacgcga tgtgattgac gccggggtta ggctgttcaa agaggccaac      720
gttgaaaaca acgagggaag acggagtaag cgcggagcaa gaagactcaa gcgcagacgg      780
agacatcgga ttcagagggt gaaaaagctg ctcttcgatt acaatctcct gaccgatcat      840
agtgagctga gcggaatcaa cccctacgag gcgcgagtga agggctttc ccagaagctg      900
tccgaagagg agttctccgc cgcgttgctg cacctggcca acggagggg ggttcacaat      960
gtaaacgaag tggaggagga cacgggcaat gaacttagta cgaaagaaca gatcagtagg     1020
aactctaagg ctctcgaaga gaaatacgtc gctgagttgc agcttgagag actgaaaaaa     1080
gacggcgaag tacgcggatc tattaatagg ttcaagactt cagattacgt aaaggaagcc     1140
aagcagctcc tgaaagtaca gaaagcgtac catcagctcg atcagagctt catcgatacc     1200
tacatagatt tgctggagac acggaggaca tactacgagg gcccagggga aggatctcct     1260
tttgggtgga aggacatcaa ggaatggtac gagatgctta tgggacattg tacatatttt     1320
ccggaggagc tcaggagcgt caagtacgcc tacaatgccg acctgtacaa tgccctcaat     1380
gacctcaata acctcgtgat taccagggac gagaacgaga gctggagta ctatgaaaag      1440
ttccagatta tcgagaatgt gtttaagcag aagaagaagc cgacacttaa gcagattgca     1500
aaggaaatcc tcgtgaatga ggaagatatc aagggataca gagtgacaag tacaggcaag     1560
cccgagttca caaatctgaa ggtgtaccac gatattaagg acataaccgc acgaaaggag     1620
ataatcgaaa acgctgagct cctcgatcag atcgcaaaaa ttcttaccat ctaccagtct     1680
agtgaggaca ttcaggagga actgactaat ctgaacagtg agctcaccca agaggaaatt     1740
gagcagattt caaacctgaa aggctacacc gggacgcaca atctgagcct caaagcaatc     1800
aacctcattc tggatgaact ttggcacaca aatgacaacc aaattgccat attcaaccgc     1860
ctgaaactgg tgccaaaaaa agtggatctg tcacagcaaa aggaaatccc tacaaccttg     1920
gttgacgatt ttattctgtc ccccgttgtc aagcggagct tcatccagtc aatcaaggtg     1980
atcaatgcca tcattaaaaa atacggattg ccaaacgata taattatcga gcttgcacga     2040
gagaagaact caaaggacgc ccagaagatg attaacgaaa tgcagaagcg caaccgccag     2100
acaaacgaac gcatagagga aattataaga acaaccggca agagaatgc caagtatctg      2160
atcgagaaaa tcaagctgca cgacatgcaa gaaggcaagt gcctgtactc tctggaagct     2220
atcccactcg aagatctgct gaataatcca ttcaattacg aggtggacgc catcatccct     2280
agatccgtaa gctttgacaa ttccttcaat aacaaagttc tggttaaaca ggaggaaaat     2340
tctaaaaaag ggaaccggac cccgttccag tacctgagct ccagtgacag caagattagc     2400
tacgagactt ttaagaaaca tattctgaat ctggccaaag gcaaggcag gatcagcaag      2460
accaagaagg agtacctcct cgaagaacgc gacattaaca gatttagtgt gcagaaagat     2520
ttcatcaacc gaaaccttgt cgatactcgg tacgccacga gaggcctgat gaatctcctc     2580
aggagctact tccgcgtcaa taatctggac gttaaagtca gagcataaa tgggggattc      2640
accagctttc tgaggagaaa gtggaagttt aagaaggaac gaaacaaagg atacaagcac     2700
catgctgagg atgctttgat catcgctaac gcggacttta tctttaagga atggaaaaag     2760
ctggataagg caaagaaagt gatggaaaac cagatgttcg aggagaagca ggcagagtca     2820
atgcctgaga tcgagacaga gcaggaatac aaggaaattt tcatcacccc tcatcagatt     2880
aaacacataa aggacttcaa agactataaa tactctcata gggtggacaa aaaacccaat     2940
```

-continued

| | |
|---|---|
| cgcgagctca ttaatgacac cctgtactca acacggaagg atgataaagg taataccttg | 3000 |
| attgtgaata atcttaatgg attgtatgac aaagataacg acaagctcaa gaagctgatc | 3060 |
| aacaagtctc cagagaagct ccttatgtat caccacgacc cacagactta tcagaaattg | 3120 |
| aaactgatca tggagcaata cggggatgag aagaacccac tctacaaata ttatgaggaa | 3180 |
| acaggtaatt acctgaccaa gtactccaag aaggataacg gaccagtgat caaaaagata | 3240 |
| aagtactatg gcaacaaact taatgcgcat ttggacataa ctgacgatta ccccaattct | 3300 |
| cgaaacaagg ttgtgaagct ctccctgaag ccttatagat ttgacgtgta cctggataat | 3360 |
| ggggtttata aattcgtcac cgtgaaaaat ctggacgtga tcaaaaagga gaactattat | 3420 |
| gaagtaaaact caaagtgcta tgaggaggcg aagaagctga agaagatctc caatcaggcc | 3480 |
| gagttcatcg cttccttcta taataacgat ctcatcaaga tcaatggaga gctttatcgc | 3540 |
| gtcattggtg tgaacaatga cttgctgaac aggatcgaag tcaatatgat agacattacc | 3600 |
| taccgggagt atctcgaaaa catgaatgat aaacggccgc ctcgcatcat caagacaatc | 3660 |
| gcatctaaaa ctcagtcaat aaaaaagtac tctaccgata tcctgggaa tctctatgaa | 3720 |
| gtgaagtcaa agaagcaccc acaaatcatt aaaaaaggtg atccgcaga agcagcagca | 3780 |
| aaggaagcag cagcaaagga agcagcagca aaggcagtcg acaccggtcc agcagctaag | 3840 |
| agagttaaac tagattagcg gccgcatcgt caggccaagc ttccatcgat agacatgata | 3900 |
| agatacattg atgagtttgg acaaaccaca acaagaatgc agtgaaaaaa atgctttatt | 3960 |
| tgtgaaattt gtgatgctat tgctttattt gtaaccatta taagctgcaa taaacaagtt | 4020 |
| aacaacaaca attgcattca ttttatgttt caggtaccga gggcctattt cccatgattc | 4080 |
| cttcatattt gcatatacga tacaaggctg ttagagagat aattggaatt aatttgactg | 4140 |
| taaacacaaa gatattagta caaaatacgt gacgtagaaa gtaataattt cttgggtagt | 4200 |
| ttgcagtttt aaaattatgt tttaaatgg actatcatat gcttaccgta acttgaaagt | 4260 |
| atttcgattt cttggcttta tatatcttgt ggaaaggacg aaacaccgag ggaagggata | 4320 |
| caggctggag ttttagtact ctggaaacag aatctactaa aacaaggcaa aatgccgtgt | 4380 |
| ttatctcgtc aacttgttgg cgagattttt gcggccgc | 4418 |

<210> SEQ ID NO 16
<211> LENGTH: 22
<212> TYPE: DNA
<213> ORGANISM: Artificial Sequence
<220> FEATURE:
<223> OTHER INFORMATION: recombinant

<400> SEQUENCE: 16
gagggaaggg atacaggctg ga                                    22

<210> SEQ ID NO 17
<211> LENGTH: 21
<212> TYPE: DNA
<213> ORGANISM: Artificial Sequence
<220> FEATURE:
<223> OTHER INFORMATION: recombinant

<400> SEQUENCE: 17
acgaacgagg gcgcggtggg t                                     21

<210> SEQ ID NO 18
<211> LENGTH: 20
<212> TYPE: DNA
<213> ORGANISM: Artificial Sequence

```
<220> FEATURE:
<223> OTHER INFORMATION: recombinant

<400> SEQUENCE: 18
ggagaccaag gcagtttttt                                           20

<210> SEQ ID NO 19
<211> LENGTH: 20
<212> TYPE: DNA
<213> ORGANISM: Artificial Sequence
<220> FEATURE:
<223> OTHER INFORMATION: recombinant

<400> SEQUENCE: 19
ggagaccacg gcaggtctca                                           20
```